United States Patent [19]
Brown

[11] Patent Number: 5,913,310
[45] Date of Patent: Jun. 22, 1999

[54] METHOD FOR DIAGNOSIS AND TREATMENT OF PSYCHOLOGICAL AND EMOTIONAL DISORDERS USING A MICROPROCESSOR-BASED VIDEO GAME

[75] Inventor: Stephen J. Brown, San Mateo, Calif.

[73] Assignee: Health Hero Network, Inc.

[21] Appl. No.: 08/958,786

[22] Filed: Oct. 29, 1997

Related U.S. Application Data

[63] Continuation-in-part of application No. 08/857,187, May 15, 1997, which is a continuation of application No. 08/247,716, May 23, 1994, Pat. No. 5,678,571.

[51] Int. Cl.⁶ .................................................. A61B 19/00
[52] U.S. Cl. ........................... 128/897; 128/905; 600/300
[58] Field of Search ............................... 128/897–98, 905, 128/668; 600/300, 451

[56] References Cited

U.S. PATENT DOCUMENTS

| | | |
|---|---|---|
| 5,307,263 | 4/1994 | Brown . |
| 5,601,435 | 2/1997 | Quy . |
| 5,619,991 | 4/1997 | Sloane . |
| 5,678,571 | 10/1997 | Brown . |

*Primary Examiner*—John P. Lacyk
*Attorney, Agent, or Firm*—Hopgood, Calimafde, Kalil & Judlowe, LLP

[57] ABSTRACT

Disclosed is a method and associated apparatus for monitoring, diagnosis and treatment of psychological and/or emotional conditions in human patients with the aid of a micro-processor-based video game.

23 Claims, 17 Drawing Sheets

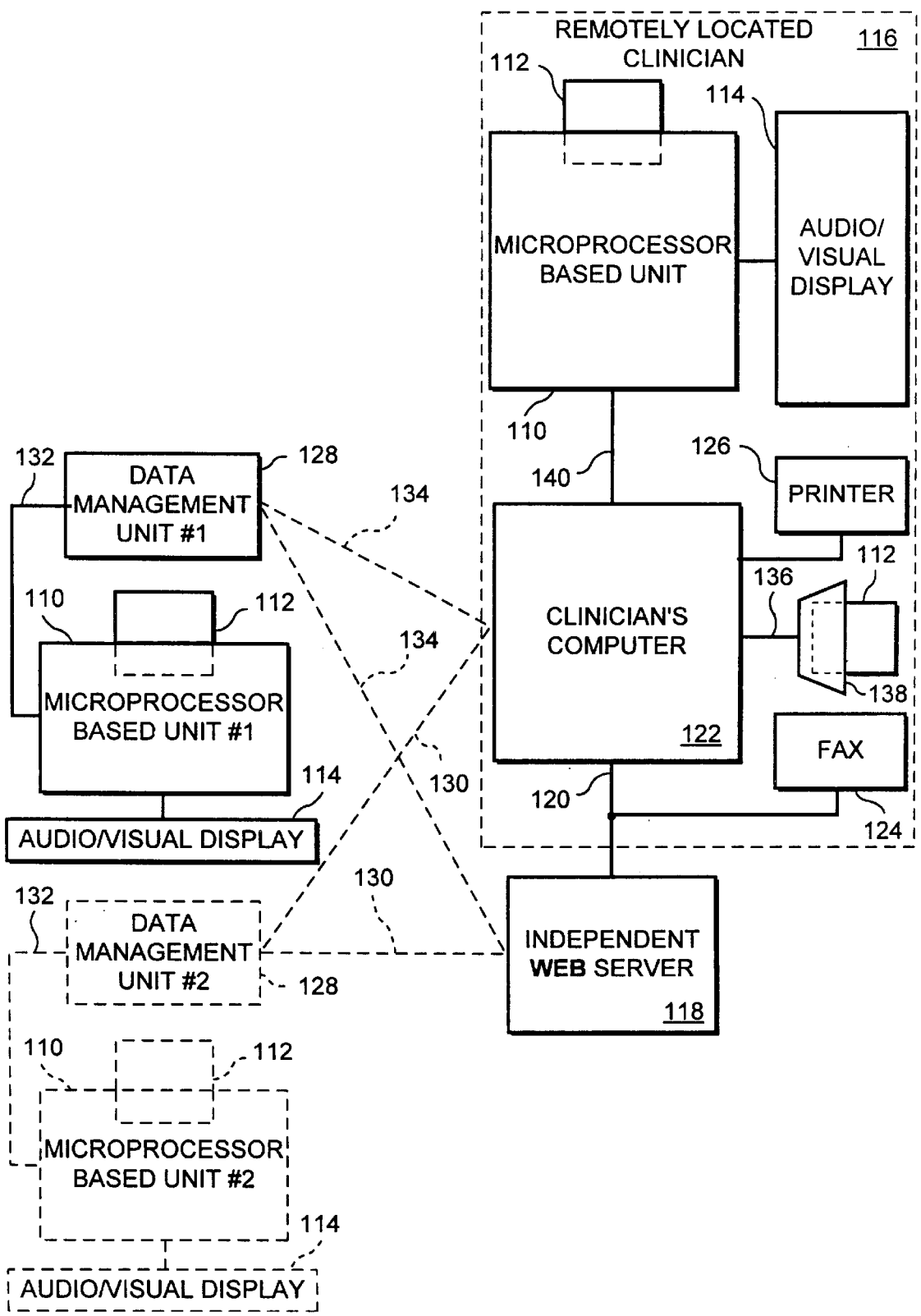
F I G. 3

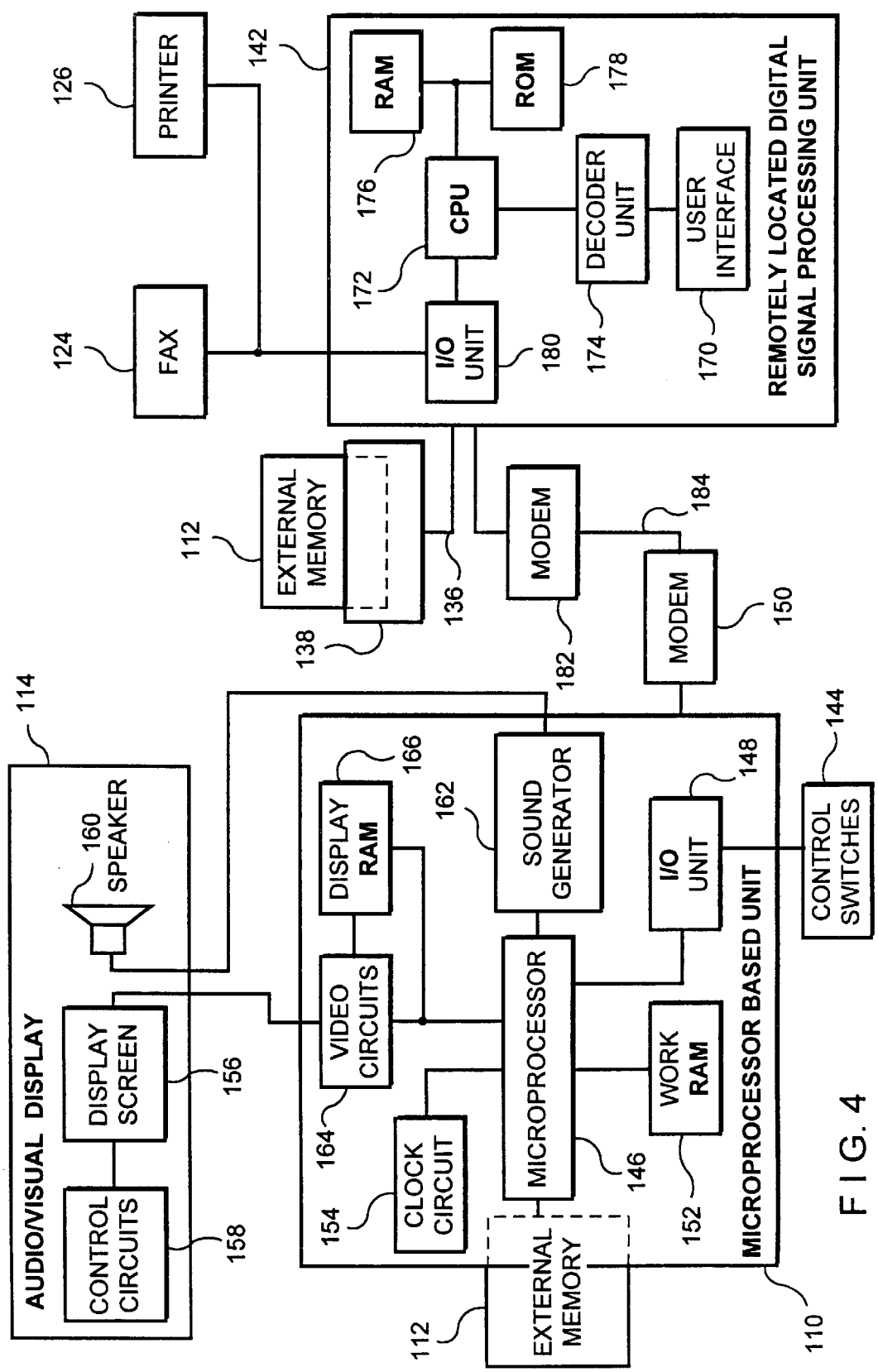
F I G. 4

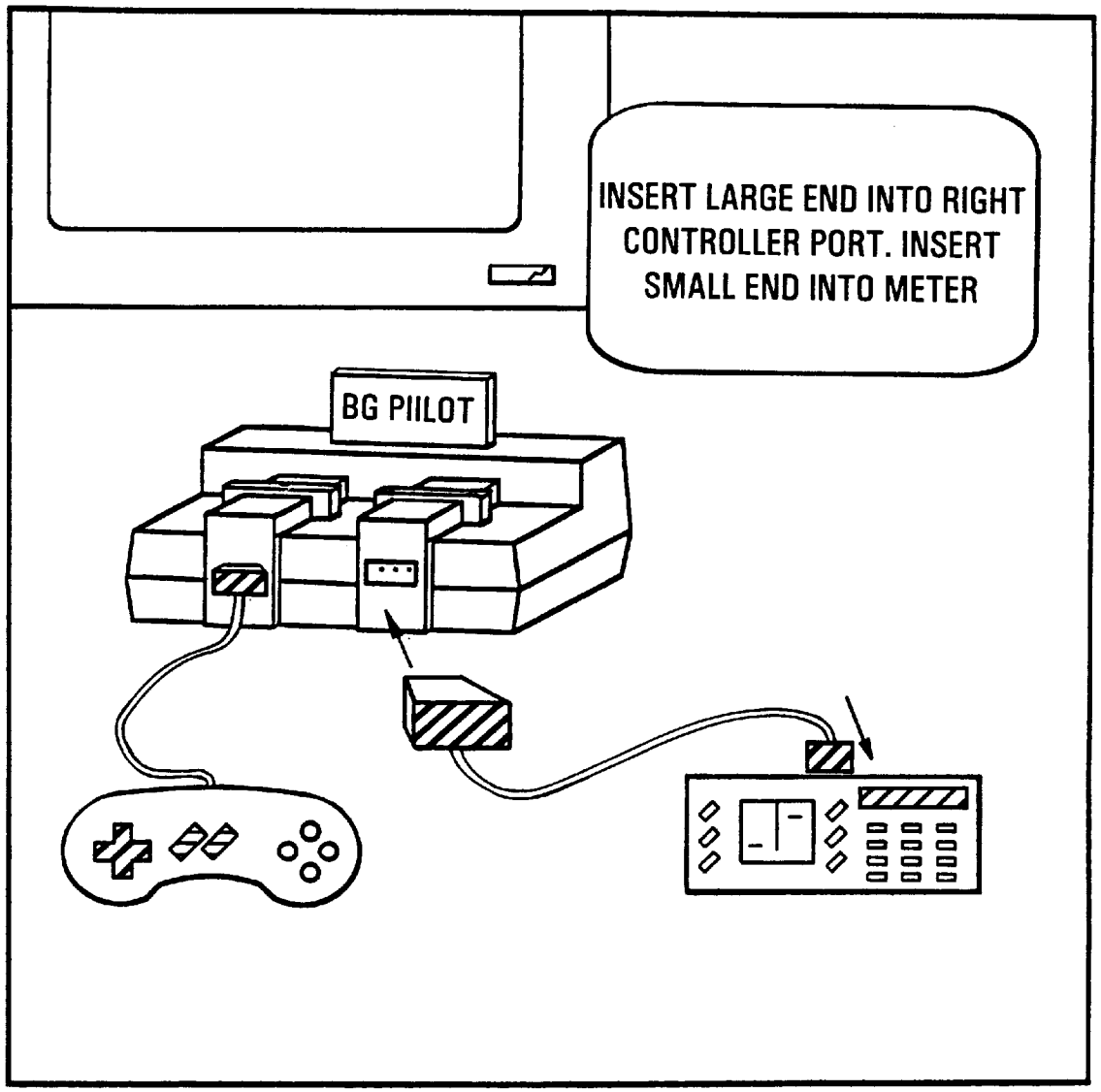
F I G. 10

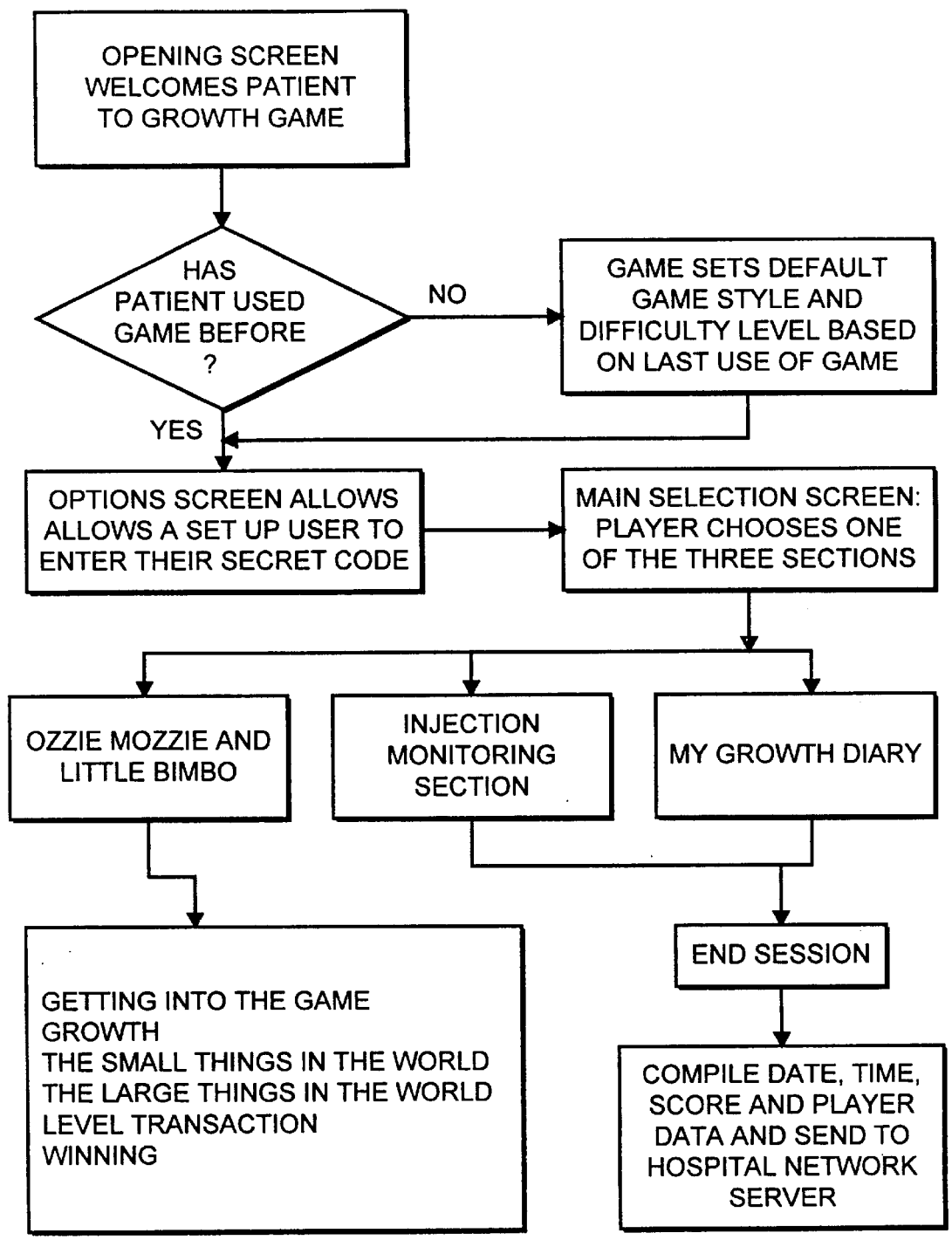
F I G. 13

METHOD FOR DIAGNOSIS AND TREATMENT OF PSYCHOLOGICAL AND EMOTIONAL DISORDERS USING A MICROPROCESSOR-BASED VIDEO GAME

RELATED CASES

This is a continuation-in-part of application Ser. No. 857,187 filed May 15, 1997, pending which is a continuation of application Ser. No. 247,716, filed May 23, 1994, now U.S. Pat. No. 5,678,571.

BACKGROUND

1. FIELD OF THE INVENTION

The present invention relates to methods and apparatus for diagnosis and treatment of psychological and/or emotional conditions in human patients with the aid of a microprocessor-based video game.

2. DESCRIPTION OF THE ART

A patient's behavioral response to his/her medical condition is evaluated and treated in conjunction with other, regular therapy and is conducted by the primary physician or health care specialist. Depending on the medical condition, a preliminary picture of the patient's emotional condition may be available to the specialist in the form of answers to questionnaires or results from a battery of tests.

This type of evaluation is currently necessary in psychological conditions such as schizophrenia, depression, hyperactivity, phobias, panic attacks, anxiety, overeating and other emotional disorders wherein a patient's maladaptive behavioral response to his/her environment is the medical condition to be treated. Currently available tests for classifying such conditions rely on the patient to perform a self-examination and to respond candidly to a series of personal questions. Since most tests differ in their basic scientific assumptions, the results obtained are not'standardized and cannot often be used to make meaningful case comparisons.

When applied to pediatric patients, problems existing in the art are amplified as compliance is not guaranteed and when the answering of questionaires is aided by an adult, the input of the adult usually hampers rather than enhances objective responses. Cohen et al., *Am. J. Diseases of Children*, 143:1229–33 (1989). Self-evaluating questionnaires that allow a child to assess his or her own situation may provide a valuable comparison between the child's view of his or her behavior and that of adults, but the dependability of these questionnaires, especially in pre-adolescent children, has not yet been determined. Braswell et al., *Cognitive Behavioural Therapy with ADHD Children*, The Guilford Press, New York (1991). Currently available methods of psychological evaluation are painstaking and tedious, involve long hours of diagnostic evaluation and are, consequently, very expensive.

Following diagnosis, the actual therapeutic changes in the patient usually occur outside of the therapy sessions as cognitive and behavioral strategies learned in therapy are applied by the patient to problems encountered in day-to-day situations. Progress is predicated to a large extent on patient cooperation, discipline and the ability to self-manage. Lack of compliance to long-term therapy regimes present a major obstacle to successful treatment. Children are a particularly difficult group of patients in this respect. Frequently, children lack the understanding, maturity and perseverance required to successfully pursue any kind of a treatment plan.

For most psychological and emotional disorders, the only available criteria for diagnosis and treatment alternatives recognized by the art is compiled in the Diagnostic and Statistical Manual of Mental Disorders, a standard classification text by the American Psychiatric Association. Such criteria are classical categorizations and very academic by nature, and are often impractical for children and uneducated adults.

For instance, Attention Deficit Hyperactivity Disorder (ADHD) is one of the most prevalent childhood psychiatric disorders characterized by behavioral problems, social maladjustment, aggression and academic difficulties, and effects 3 to 5 percent of American children. Erickson, M., *Behavior Disorders of Children and Adolescents*, Prentice Hall, Englewood Cliffs, N.J. (1987); Barkley, R., *Attention Deficit Hyperactivity Disorder*, The Guilford Press, New York (1990). ADHD is diagnosed as a debilitating disease of children with negative consequences into adulthood if untreated. However, even with proper and early diagnosis, reliable treatment still does not exist for ADHD.

In the United States, as many as 750,000 children take psychostimulant medication such as methylphenidate, dextroamphetamine or Ritalin® (CIBA Pharmaceuticals) each day for ADHD. Unfortunately, almost 25 percent of those children experience no behavioral improvement from such drugs, and almost half of the remaining children receive only marginal benefits. Greenhill, L., *Psychiatric Clin. of N. America*, 14:1–25 (1992). Thus, a need exists in the art for methods and apparatus designed for diagnose of ADHD and sub-categories of ADHD, namely those children who have ADHD but are not responsive to psychostimulants.

Management techniques other than maintenance with psychostimulants exist and involve behavior therapy such as changing the family and school environments. But, these social changes are a daunting task, and a need also exists in the art for methods and apparatus designed for ADHD children using efficient, computer-based education systems which convey assessment data to clinicians to monitor and provide healing support.

There is also a wide variety of maladaptive conditions other than the above-mentioned psychological disorders, requiring extensive self-help and self-treatment. These conditions include compulsive behaviors and addictive, substance abuse. Most common examples are gambling, smoking and alcoholism. At the present time treatment for these medical conditions involves counseling, distraction techniques and chemical replacement therapy. Ultimately, however, all of these methods depend on the cooperation of the patient and a large dose of self-motivation. This is especially important when the patient is in his or her own surroundings where the objects of their addiction or compulsion are easily accessible.

Some attempts have been made at using computers to diagnose and educate patients about their medical condition. Typically these attempts have produced questionnaires which can be filled out on a computer, or educational programs telling the patient more about his or her medical condition. Unfortunately, these projects stop short of being sufficiently adapted to patient needs, and a need exists in the art for a method and apparatus for diagnosis and treatment of psychological and/or emotional conditions in human patients with the aid of a micro-processor-based video game.

OBJECTS OF THE INVENTION

It is an object of the present invention to provide a method for monitoring, diagnosing and treating psychological and emotional disorders using a microprocessor-based system.

Another object of the invention is to provide methods for monitoring, diagnosing and treating psychological conditions such as schizophrenia, and behavioural disorders such as depression, hyperactivity, phobias, panic attacks; anxiety, overeating, obsessive-compulsive behaviors, addictiions and substance abuse, using a microprocessor-based system.

A further object of the invention is to provide methods for diagnosing psychological and emotional disorders in children using a video game.

Yet another object is to provide a method and associated apparatus for diagnosis of psychological and emotional disorders in children using a video game.

Still another object is to provide methods and associated apparatus for diagnose of ADHD and sub-categories of ADHD, namely those children who have ADHD but are not responsive to psychostimulants.

Another object is to provide a means for linking the inventive system to a network with a peripheral server capable of receiving, storing, processing, analyzing and exchanging data within the network.

These and other objects and advantages will become more apparent after consideration of the ensuing description and the accompanying drawings.

SUMMARY OF THE INVENTION

One aspect of the invention is a microprocessor controlled video game system capable of receiving commands generated by a user suffering a psychological disorder. The system is capable of generating complex multidimensional information displays as a first series of outputs to the user characterized by indicia configured and presented in a manner directed to aid in the diagnosis of the psychological disorder. The system comprises a means for control which uses a stored protocol directed to the specific psychological disorder. The protocol is comprised of display controlling functions which include programming commands for controlling one or more graphical elements presented on the displays.

The diagnostic system also has means for inputting user generated commands which are interactively entered in response to the first series of outputs and means for relaying a second series of outputs to a health care professional such as a physician or nurse. The second series of outputs are specifically configured to provide a presentation of the user's inputs to the health care professional for diagnosis of the psychological disorder in question.

In the diagnostic system, the protocol of display controlling functions includes programming commands for manipulating at least one graphical character presented on the displays. The stored protocol is specifically configured to provide a test battery of continuous performance tasks through displays to the user, and can further comprise a data collection subsystem for storing and analyzing the user's inputs responsive to the battery and relaying the analytic results via the second series of outputs to the health care professional for diagnosing the psychological disorder.

The system can further comprise a means for linking it to a network. The linking means comprises a means for interfacing the microprocessor to the network and at least one peripheral server linked to the network, with the server being capable of receiving the inputs and outputs and capable of exchanging data within the network. The server can comprise a means for receiving, a means for storing and a means for processing the inputs and the outputs. The network server can further comprise a second microprocessor controlled data processing unit in communication with the system, wherein the second microprocessor controlled data processing unit is capable of processing and exchanging data with the system.

The psychological disorders contemplated herein can include ADHD, schizophrenia, depression, hyperactivity, phobias, panic attacks, anxiety, overeating, compulsive behaviors, addictions and substance abuse. However, this is not a comprehensive list, anu those skilled in this art and the medical arts could easily adapt the disclosed invention to other similar disorders and obtain substantially equivalent results.

When the psychological disorder for diagnosis is ADHD, the battery further comprises auditory and visual delayed reaction time tests for attention, and the subsystem comprises an administrator program for configuring the tests.

Another aspect of the inventions is a method for diagnosing a psychological disorder in a human patient and begins with encoding electronic instructions for an interactive video game configured for the psychological disorder and comprised of a microprocessor controlled system capable of receiving input data from and providing an interactive display to the patient, the system further comprising a stored protocol directed to diagnosis criteria for the psychological disorder. Next, the electronic instructions are loaded into the microprocessor-based system, followed by instructing the human patient on how to use the microprocessor-based unit to play the interactive video game. The inputted data from the patient is collected and analyzed based on the protocol to arrive at the diagnosis. The method can include analysis of the input data from the patient to categorize whether the patient is responsive to maintenance psychostimulants.

The invention also encompasses a microprocessor controlled video game system directed to the treatment of a psychological disorder. The treatment system comprises means for controlling the system using a stored protocol directed to the psychological disorder in question, comprised of display controlling functions wherein the functions include programming commands for controlling one or more graphical elements presented on the displays. The treatment system also has means for inputting the user generated commands which are interactively entered by the user in response to the outputs presented on the displays. It also has means for interpreting the inputted user generated commands, then applying the stored protocols to the inputted commands, and based thereon, controlling the output to the display wherein the output is specifically configured to provide a presentation to the user that enhances the treatment of the psychological disorder. In the therapeutic system, the stored protocol can also be configured to provide experiential education specific for the psychological disorder.

When the therapeutic system is based on treatment for ADHD, and the stored protocol is configured to provide opportunities to practice focus of attention and control of impulses, supportive and performance feedback, and general information about ADHD and its treatment.

Also provided is a method for treatment of a psychological disorder in a human patient which initiates with providing the patient with a microprocessor controlled video game capable of interacting with the patient to obtain personal data related to the psychological disorder. The obtained personal data is transmitted to another microprocessor controlled system capable of collecting and analyzing the data. A compiled report based on the collected and analyzed data is automatically generated by the system and criteria specific to the patient are generated to implement an optimum treatment regimen for the psychological disorder. When dealing with ADHD, the treatment regimen includes management of psychostimulant medication.

The invention also encompasses a method for monitoring a psychological disorder in a human patient comprising the steps of encoding electronic instructions for an interactive video game configured for the psychological disorder to be monitored. The video game comprises a microprocessor controlled system capable of receiving input data from and providing an interactive display to the patient. The system further comprises a stored protocol directed to criteria for monitoring the specific psychological disorder of the patient. The monitoring method further comprises the steps of loading the electronic instructions into the microprocessor-based system, instructing the patient on how to use the microprocessor-based unit to play the interactive video game; and monitoring input data from the patient. The stored protocol is specifically configured to provide a test battery of continuous performance tasks to the patient through the interactive display, and the input data from the patient in response to the test battery is monitored to facilitate diagnoses and treatment of the psychological disorder.

BRIEF DESCRIPTION OF THE DRAWINGS

FIG. 3 is a block diagram that illustrates microprocessor-based patient units connected in signal communication with a clinician's computer system and/or an independent web server through the internet, for collection and analysis of diagnostic data originating with a large number of patient units.

FIG. 4 is a block diagram illustrating in greater detail the basic structure of a micro-processor-based patient unit and a digital signal processor of a type that can be used by the clinician's PC, an intranet at the clinician's site or by an independent web server.

FIGS. 8, 9 and 10 are exemplary screens of a video game for self-treatment of diabetes.

FIG. 13 is a flowchart for the Growth Game.

DETAILED DESCRIPTION OF THE INVENTION

Figure 1:
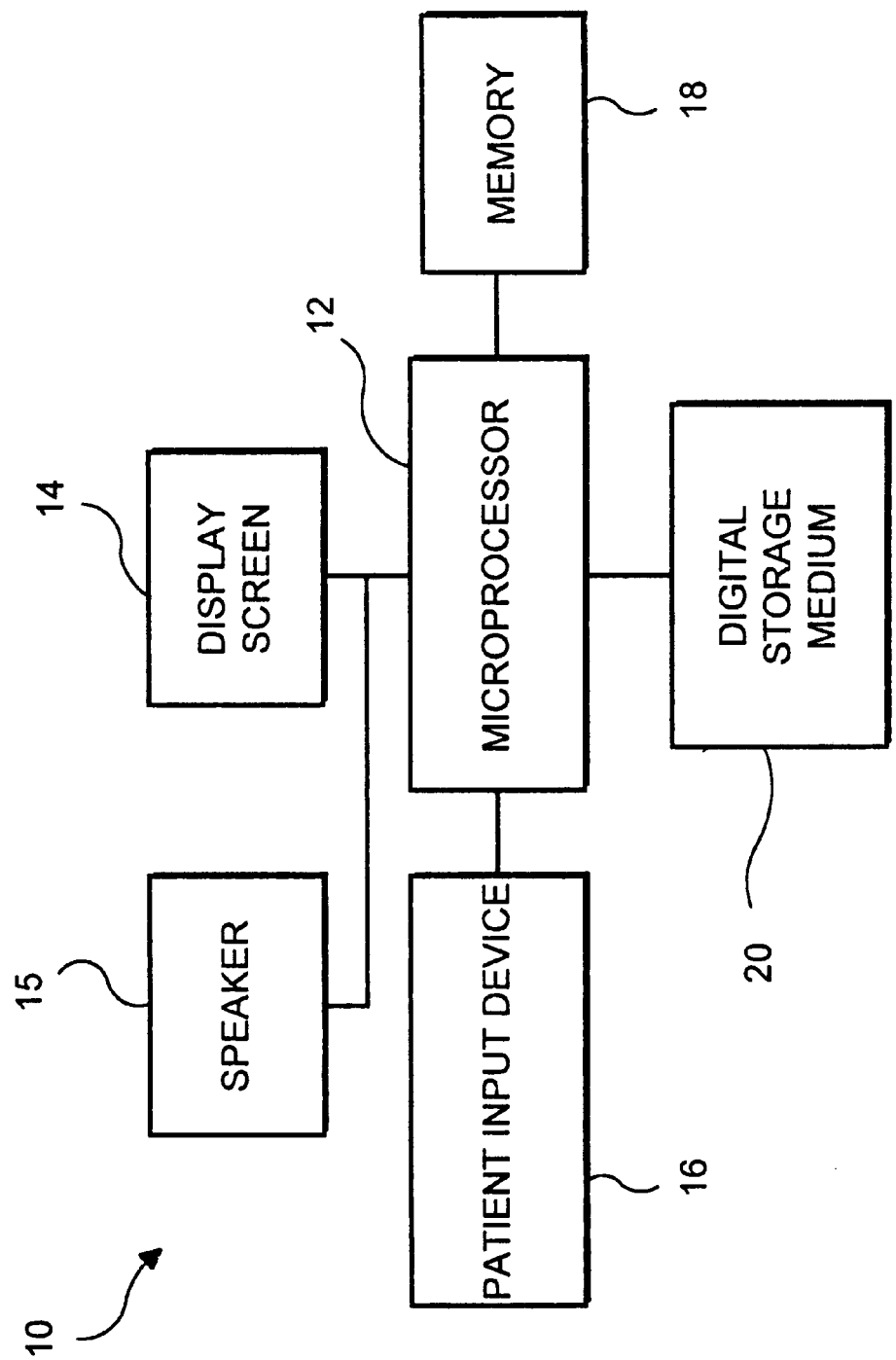
FIG. 1 is a block diagram depicting the apparatus system employed in the method according to the invention.

FIG. 1 shows a block diagram representing a typical embodiment of a computer or micro-processor-based unit 10 capable of supporting video games for patient treatment. At the heart of unit 10 is a microprocessor 12. In addition to operations necessary to run unit 10, microprocessor 12 can process video data. In more complicated systems, the tasks of microprocessor 12 can be performed by a number of microprocessors. In the most preferred embodiment microprocessor 12 is a SUPER NINTENDO™ microprocessor.

A display unit or screen 14 is connected to microprocessor 12. The resolution and size of display screen 14 are sufficient to project visual images generated by video games. Screen 14 can be a high-resolution video monitor or television screen. A speaker 15 for producing sounds associated with video games is hooked up to microprocessor 12 as well.

A patient input device 16 is also connected to microprocessor 12. Input device 16 can be a keyboard, joystick, mouse, button, trigger, light-pen, or the like, or combinations of these devices. A suitable choice of input device 16 is made based on the video game displayed on display screen 14 and the medical conditions of the human patient. The selected input device 16 will thus permit the patient to actively participate in the video game.

Additionally, microprocessor-based unit 10 has a memory 18, which is in communication with microprocessor 12. Memory 18 contains data required by microprocessor 12 to operate unit 10. While in the exemplary embodiment illustrated in FIG. 1, memory 18 consists of a single unit, configurations with many memory units of different types are possible.

Unit 10 is also connected to a digital storage medium 20 and appropriate data reading devices (not shown). Digital storage medium 20 can be a hard-disk, a floppy disk, a compact disk (CD), a cartridge, a network storage unit, or any other convenient medium capable of storing electronic instructions for running a video game on unit 10. Storage medium 20 can be a high-storage capacity CD disk. The ability to hold a large amount of data is a prerequisite for storing large video game programs.

Figure 2:
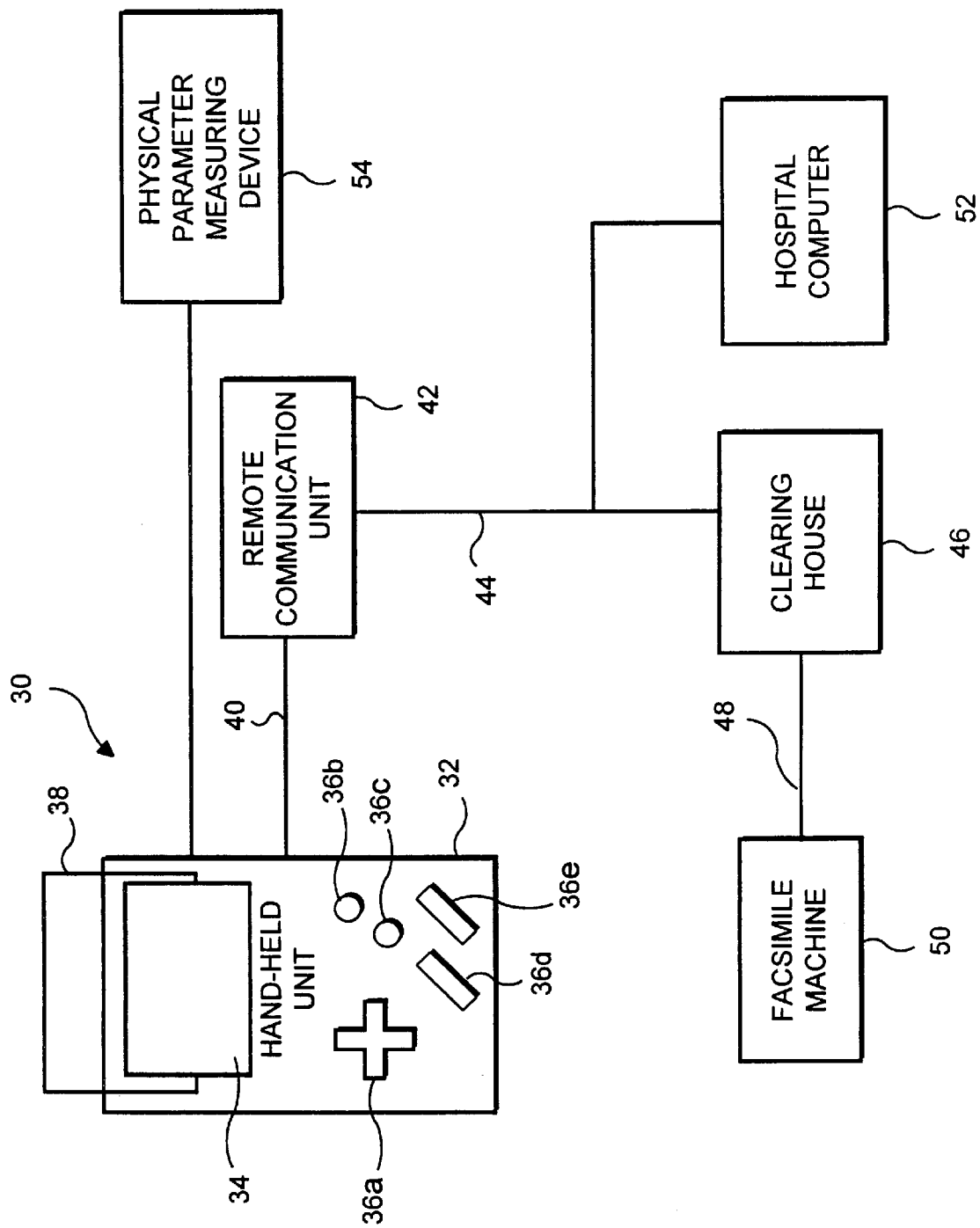
FIG. 2 is a block diagram of a system employing a hand-held microprocessor unit for implementing the method and system of the present invention.

The block diagram of FIG. 2 shows a particularly convenient embodiment for implementing the diagnosis and treatment method. A hand-held microprocessor unit 30 is equipped with a video display 34 and a number of input switches or keys 36a, 36b, 36c, 36d and 36e, which are mounted on a housing 32. A set of components including a microprocessor, memory circuits and circuitry that interfaces keys 36a, 36b, 36c 36d and 36e with the microprocessor is installed inside housing 30 but not shown in FIG. 2. Stored in the memory of programmable hand-held microprocessor unit 30 is a set of electronically encoded program instructions. These instructions establish a data protocol that allows hand-held microprocessor unit 30 to perform digital data signal processing and generate desired data or graphics for display on display unit 34 when a program cartridge 38 is inserted into a slot or other receptacle in housing 32. That is, cartridge 38 of FIG. 2 includes read-only memory data encoding the instructions for playing a particular video game.

Hand-held microprocessor unit 30 can be, by way of example, the compact game system manufactured by Nintendo of America, Inc. under the trademark "GAME BOY". This device is particularly simple. Furthermore, unit 30 is hooked up to a remote communication unit 42 via a connection cable 40. Preferably unit 42 can be a modem capable of communicating over telephone lines or a radio-frequency transceiver capable of wireless sending and receiving of information. Other telecommunications devices known to the art can also be used. By way of example, the embodiment shown in FIG. 2 has high-speed modem unit 42.

A communication line 44, in this event a telephone line, connects unit 42 to a data clearing house 46 and hospital computer 52. This set-up establishes an efficient data pathway from hand-held microprocessor unit 30 to clearing house 46 and hospital computer 52. Clearing house 46 is capable of classifying data and sending appropriate messages concerning the patient's medical condition to a health care professional or physician In the preferred embodiment clearing house 46 is connected by transmission line to a facsimile machine 50 standing in the office of a physician or health care professional.

A physical parameter measuring device 54, such as a glucose blood meter or a respiratory flow meter, is also connected to hand-held unit 30. Device 54 is designed for patient self-monitoring while playing a video game. For this purpose device 54 is capable of downloading measurement data into hand-held unit 30. Appropriate choice of device 54 is made by the physician depending on the other hardware and intended video game for patient treatment.

FIG. 3 illustrates one embodiment of a diagnostic measurement system configured in accordance with the invention. The depicted embodiment includes a programmable microprocessor-based unit 110 that includes a receptacle for receiving an external memory unit 112, which can be easily inserted and removed from microprocessor-based unit 110. Removable memory unit 112 includes a digital storage medium for storing program instructions that control the operation of microprocessor-based unit 110 and, in addition, allows storage of diagnostic test information that is generated during operation of microprocessor-based unit 110 for diagnostic assessment of a psychological condition.

Various storage media known to those skilled in the art can be used as the digital storage medium of external memory unit 112. For example, conventional read on, memory (ROM) can be employed for storage of program instructions that are not changed or altered when external memory 112 is reconfigured for a different patient or reconfigured for measurements relating to a different type of psychological condition. Optically scanned memory such as currently available compact disc memory can also be employed. In addition, various types of erasable read-only memory and random access memory (RAM) having a battery back-up can be used to provide a storage medium for program instructions that may be changed when external memory 112 is configured for use with a different patient or for the diagnostic assessment of the different psychological condition. Erasable read-only memory or battery backed-up RAM also can be used for storage of information gathered when microprocessor-based unit 110 is operated to gather diagnostic measurement information that relates to one or more psychological conditions. Moreover, in newly developing technologies such as audio/video interactive television and networks for digital communications program instructions can be transmitted to micro-processor-based unit 10 and stored in random access memory.

As is indicated in FIG. 3, micro-processor-based unit 110 is interconnected with an audio/visual display unit 114. During operation of the invention for diagnostic assessment of psychological conditions, microprocessor-based unit 110 generates audio and video signals that are presented to the patient or system user by audio/visual display unit 114. The audio/visual presentation is controlled by program instructions that are either stored in external memory 112 or are otherwise supplied to microprocessor-based unit 110. In the disclosed embodiments, the visual presentation is structured to elicit responses from the user of microprocessor-based unit 110 (e.g., a patient or research subject) that provide that diagnostic measures relating to a particular psychological condition.

In that regard, the preferred embodiment disclosed herein are arranged for diagnostic assessment of Attention Deficit Hyperactivity Disorder (ADHD). Upon understanding the operation of the invention and the various manners in which it can be configured, it will be recognized that the invention can be used in the diagnoses of various other psychological conditions and behavior patterns, including anxiety disorders, depression, schizophrenia, addiction, and weight controlling disorders.

A primary advantage of the invention is the ability to conduct a diagnostic assessment procedure in an environment other than the office of a clinician or other health care facility. This particular aspect of the invention can be important with respect to diagnosing psychological conditions that are highly situation-dependent. Further, since it is not necessary for a clinician to be present when a diagnostic assessment procedure is executed, the costs of diagnoses and treatment is reduced. For example, during a clinical session, a clinician can instruct a patient or subject in the use of the invention for diagnostic assessment of a particular psychological condition. The patient or user then uses microprocessor-based unit 110, a suitably programmed external memory 112, and an audio/visual display unit 114 between clinical sessions to gather appropriate diagnostic measurements while the subject is in suitable environmental surroundings (e.g., at home, school, or the workplace). Information gathered during the diagnostic assessment is then made available to the clinician for consideration and analysis.

There are two basic ways in which information that relates to the results of the diagnostic assessment can be conveyed to a clinician or other person who serves as an administrator for the conduction of the diagnostic assessment. These same techniques are employed for establishing the diagnostic procedure (i.e., storing suitable program instructions in external memory 112). The first technique for transferring test results or programming micro-processor-based unit 110 (e.g., external memory unit 112) involves data transmission between processor-based unit 110 and a remotely located clinician's office (or other health care facility) or, alternatively, a remotely located facility that stores the information for subsequent analysis and transmission to the clinician. In the second technique, microprocessor-based unit 110 (or external memory unit 112) is physically transferred between the site at which the diagnostic assessment is made and the clinician's facility or other remote location.

With respect to the first information transfer technique, FIG. 3 schematically illustrates arrangement of the invention for remote exchange of data and information between a microprocessor-based unit 110 and either a remotely located clinician 116 or, for example, a web server 118 through the internet which is independent of the clinician. In such an arrangement, independent web server 118 includes one or more digital signal processors sufficient for gathering diagnostic measurement information from a relatively large number of micro-processor-based diagnostic tools (represented by micro-processor-based unit #1 and micro-processor-based unit #2 of FIG. 3.

A communication link 120 is shown in FIG. 3 between independent web server 118 and the clinician's remote location 116 to indicate transfer of information electronically or by other signal transmission means. Specifically, data and information can be transferred electronically between web server 118 and a clinician by various conventional data transmission systems, including those implemented through the internet such as via HTTP and the world wide web, etc. As is indicated in FIG. 3, the signals sent by web server 118 to the clinician's facility 116 can be coupled to devices such as the clinician's computer 122 and/or the clinician's facsimile machine 124. Signals transmitted to the clinician's computer 122 can be stored with or without additional processing.

In the same regard, analytical signal processing of the diagnostic assessment data gathered by microprocessor-based unit can be performed at various stages of information transmission between patient and clinician. For example, data processing can be performed in microprocessor-based unit 110, the clinician's computer 122, web server 118 and/or the hereinafter described data management unit 128. In any case, when the diagnostic information is transmitted to the clinician's facility, it can be displayed on a display unit of the clinician's computer 122 (not shown in FIG. 3) printed by a printer 126 that is connected to computer 122, or processed by other devices that are peripheral to the clinician's computer 122. It is to be noted that the clinician's PC 122 at facility 116 can itself be programmed to be a web server with proper hardware configurations as will probably be more practical with large numbers of patients and for multi-clinician-based hospitals.

With continued reference to the embodiment of the invention shown in FIG. 3, signals representative of information gathered during a diagnostic assessment procedure (and other signals appropriate to system operation) are coupled to (or from) independent web server 118 and microprocessor-based diagnostic unit 110 via a data management unit 128 and a communication link 130. Like communication link 120, which provides signal transfer between web server 118 and the clinician's facility 116, communication link 130 can be of several different types. In some instances, communication link 130 will be a signal path established by a telephone system. Alternatively, RF signal transmission can be employed. Communication link 130 also can be established through the use of specialized digital networks, including recently developed interactive audio/video systems such as those operated in conjunction with cable television.

In the arrangement of FIG. 3 each depicted data management unit 128 is interconnected with its associated microprocessor-based unit 110 by a cable 132 that includes electrical conductors for carrying signals between the two units. In each arrangement of the invention, data management unit 128 provides the signal processing that is necessary for interfacing micro-processor-based unit 110 with communications link 130 and/or a communications link 134. Communications link 134 provides for transmission of signals between micro-processor-based unit 110 and the clinician's remote location 116 (e.g. coupling of signals to and from the clinician's computer 122). Like the previously discussed communication links 120 and 130, communication link 134 can be realized in a variety of ways.

Because of the wide range of communication links 130 and 134 that are available for practice of the invention, data management 128 will take on various forms and configurations. For example, in an arrangement of the invention in which communications link 130 and/or 134 is a signal path established by a conventional telephone system, data management unit 128 will include a modem and will operate to perform the signal processing necessary to transmit information to independent web server 118 and/or the clinician's remote location 116. In some arrangements of the invention, the signal processing required for modem data transmission will be implemented by a microprocessor unit that is incorporated in data management unit 128. In other situations, the microprocessor of processor-based unit 110 can be employed to perform the signal processing necessary for modem signal transmission. Similarly, the hardware associated with modem transmission (e.g. telephone line connection) can be included in data management unit 128 or incorporated in microprocessor-based unit 110.

FIG. 3 also indicates one manner in which the invention can be employed for remote administration of diagnostic assessment of psychological conditions without the need for data management unit 128 and communication links 130 and 134. In particular, in the arrangement of FIG. 3, an external memory unit 112 can be inserted in a receptacle 138 that electrically connects external memory unit 112 to the clinician's computer 122 via a cable 136. With an external memory 112 connected in this manner, a clinician or other administrator of the diagnostic assessment to be performed can operate computer 122 to store program instructions appropriate for the diagnostic procedure in an external memory unit 112. The programmed external memory unit 112 can be given to a patient or subject at the end of a clinical session or transmitted to the patient or subject by other appropriate means. The patient or subject can subsequently insert the programmed external memory unit 112 in a microprocessor-based unit 110 that is located at the patient's home or some other location at which the diagnostic procedure will be executed. Signals representative of the diagnostic information gathered during the procedure are stored in external memory unit 112 when microprocessor unit 110 implements the diagnostic assessment procedure. External memory unit 112 is then returned to the clinician, inserted into receptacle 138 and the clinician's computer 122 is used to retrieve the diagnostic information stored in the external memory unit 112. In situations in which program instructions and diagnostic results are stored internally in microprocessor-based unit 110 (i.e. without use of an external memory unit 112), the entire micro-processor-based unit can be taken to the clinician's office. Information relating to diagnostic assessment results can then be unloaded to the clinician's computer 122 and, if desired, program instructions can be downloaded to the microprocessor-based unit 110 for administering further diagnostic assessment.

As also is shown in FIG. 3, in most applications of the invention, an additional microprocessor-based unit 110 and audio/visual display unit 114 will be located at the clinician's office or other facility. In the arrangement shown in FIG. 3, the additional microprocessor-based unit 110 is directly connected to the clinician's computer 122 by an electrical cable 140 to allow signal transmission between the microprocessor-based unit and computer 122. Providing a microprocessor-based unit 110 and audio/visual display unit 114 at the clinician's location allows a patient or subject to be instructed in the use of the system and also allows the administration of diagnostic assessment procedures at the clinician's facility, if desired.

FIG. 4 depicts a detailed block diagram of a microprocessor-based unit 110 that can be employed in the practice of the invention and an associated audio/visual display unit 114. Also shown in FIG. 4 is a basic block diagram of a remotely located digital signal processing system 142 which typifies the arrangement of web server 118 and computer 122 of FIG. 3. As is indicated in FIG. 4, signals supplied by one or more control switches 144 are coupled to a microprocessor 146 of microprocessor-based unit 110 via an input/output circuit 148. Also interconnected with input/output unit 148 of microprocessor-based unit 110 is an external modem 150, which serves as data management unit 148 (FIG. 3) for the depicted arrangement. Although not indicated in FIG. 4, it will be understood by those skilled in the art that interconnections such as the connection shown between microprocessor 146 and input/output unit 148, generally include a data, address, and control bus.

With continued reference to microprocessor-based unit 110 of FIG. 4, the depicted microprocessor 146 is interconnected with the receptacle that receives an external memory unit 112 so that microprocessor 146 can access program instructions stored in external memory unit 112 and store diagnostic assessment results in external memory 112. As previously mentioned, program instructions can be provided to a microprocessor-based unit 110 via a digital signal communications system, instead of an external memory unit 112. In such arrangements, digital signals supplied by a system such as cable television or a digital communications can be coupled to microprocessor 146 via input/output unit 148 or other conventional signal processing arrangements.

In the arrangement of FIG. 4, a random access memory 152 is interconnected with and is used by microprocessor 146 to implement a desired diagnostic assessment procedure and perform any desired analysis of the gathered diagnostic data. In addition, random access memory 152 can be used for storing program instructions that are supplied to an embodiment of the invention that does not employ an external memory unit 112 (i.e. an embodiment in which program instructions are supplied via a digital signal communications system). A clock circuit 154 is provided to allow microprocessor 146 to store date and time signals in situations in which date and time tags are to be included with the gathered diagnostic data.

Although not specifically shown in FIG. 4, microprocessor-based unit 110 generally includes an internal read-only memory for storing various program instructions and data that are not unique to a particular diagnostic assessment procedure or other application for the microprocessor-based unit 110.

The audio/visual display unit 114 that is shown in FIG. 4 corresponds to a video monitor that includes a display screen 156, control circuitry 158, and a speaker 160. In an arrangement of this type, microprocessor 146 of microprocessor-based unit 110 controls the operation of a sound generator 162 and video circuits 164 in accordance with the program instructions stored in external memory 112. A display random access memory 166 is used to store and format video signals which are coupled to display screen 156 of audio/visual display unit 114. Music, synthesized speech, and other sounds generated by sound generator 162 are coupled to speaker 160. Control circuit 158 includes the circuitry necessary for adjusting volume and display quality as well as the circuitry for driving the display screen. In other arrangements, a television set may be used as audio/visual display unit 114, with microprocessor-based unit 110 supplying an appropriate modulated rf signal or being connected to the television set video and audio inputs.

It will be recognized by those of skill in the art that a diagnostic tool that corresponds to micro-processor-based unit 110 of FIGS. 3 and 4 can be easily realized using conventional microprocessor design techniques and components. It also will be recognized that various commercially available devices can be adopted for use as a microprocessor-based unit 110 of this invention. In that regard, in the currently preferred embodiments of the invention, the microprocessor-based unit 110 is a compact video game system, with external memory unit 112 being configured to correspond to the type of game cartridge that is used with that particular video game system. As stated above, a handheld video game system such as the compact video game system marketed by Nintendo of America, Inc. under the trademark "GAME BOY" can be used to realize, in unitary form, micro-processor-based unit 110, audio/visual display unit 114, and control switches 144 of the arrangement shown in FIG. 4.

In other applications of the invention, a more "desk top" type of video game system such as the "SUPER NINTENDO ENTERTAINMENT SYSTEM" or "NES" video game is used. In those situations, control switches 144 correspond to the video game controller and audio/visual display unit 114 is a conventional television set or video monitor. The less compact video game systems often are advantageous because the external memory unit (game cartridge) has greater memory capacity than the corresponding memory of handheld units; the microprocessor has superior processing capability; and relatively high-quality sound and graphics can be achieved.

Regardless of the type employed, there are many advantages to using a video game system in the practice of the invention. Of prime importance, video game systems enjoy widespread popularity and, hence, low cost. In many cases, the user of a diagnostic assessment system that is constructed in accordance with the invention may already own or have access to a video game system. In addition, video game systems are simple to use. Therefore, little time is required for instructing a patient or other system user in how to operate the system for performance of a particular diagnostic assessment. Even further, adapting a video game system for use with the invention provides a convenient way for realizing diagnostic assessment procedures that are presented in game-like format with animation or other graphics that provide motivation for all age groups while gathering needed diagnostic data. The cumulative effect is achievement of an unobtrusive test and diagnosis arrangement that is acceptable to patients and other subjects and can be used in many environments.

Referring again to FIG. 4, it can be recognized that the depicted remotely located digital signal processing unit 142 corresponds to a wide range of computational arrangements, including the clinician's computer 122 and the previously discussed, more complex, web server 118 of FIG. 3. In the arrangement depicted in FIG. 4, a user interface 170 is connected in signal communication with a central processor unit 172 via a decoder circuit 174. Random access memory 176 and read-only memory 178 are accessed by central processor unit 172 of digital signal processing unit 142 during execution of the various programs and procedures used in carrying out the invention. An input/output unit 180 acts under the direction of central processor unit 172 to provide signals to a facsimile unit 124 and printer 126. As also is indicated in FIG. 4, signals can be provided to central processor unit 172 via input/output unit 180 by a modem 182. In the arrangement shown, a communication link 184 interconnects modem 182 with modem 150 to thereby allow the depicted digital signal processing system to receive diagnostic test information from the depicted microprocessor-based unit 10. As also is indicated, input/output unit 180 is connected to a receptacle 138, which as was described relative to FIG. 3, allows the digital data processing system to access storage addresses within an external memory unit 112 that is connected to receptacle 138.

As shall be described in more detail, an administration program that is executable by digital signal processing unit 142 includes a program module that allows program instructions to be stored in an external memory unit 112 to establish a desired diagnostic assessment procedure. Execution of another module of the administration program by digital signal processing unit 142 allows the retrieval of diagnostic test data stored in external memory unit 112 when a diagnostic assessment procedure was conducted (i.e. when a patient or user executed a diagnostic procedure in accordance with the procedure).

The currently preferred embodiments of the invention utilize a microprocessor-based unit 110 that corresponds to the previously mentioned SUPER NINTENDO ENTERTAINMENT SYSTEM, with the invention being realized for diagnostic assessment of attention deficit hyperactivity disorder. In the current realization of the invention, program instructions for a battery of separate tests that assess various aspects of a juvenile's attention are stored in external memory unit 112. Two basic types of tests are employed— (1) tests that include a series of delayed reaction tasks and tests that include a series of continuous performance tasks. In the delayed reaction tasks, programmable microprocessor-based unit 110 operates to generate an audible and/or visual warning signal to alert the user that the microprocessor-based unit soon will produce an audible and/or visual trigger stimulus. When the trigger stimulus is generated, the patient or user activates a designated switch or control of microprocessor-based unit 110 (e.g., a switch or control included in control switches 144 of FIG. 4).

In current practice, the clinician or other administrator of the diagnostic assessment procedure can select one or more audio delayed reaction tests and/one or more video delayed reaction tests when establishing a battery of tests for a particular patient or user. As shall be described in more detail below, the clinician establishes the battery of tests by executing a computer program, which also allows the clinician or administrator to establish the sequence in which various tests will be administered and, for each audio or visual delayed reaction test, select both the number of trigger stimuli to be generated and a time delay range. The time delay range establishes the upper and lower bounds of the delay between warning stimuli and trigger stimuli. The specific delay between a particular warning stimulus and its associated trigger stimulus is selected randomly by microprocessor-based unit 110 when the delayed reaction test is conducted.

Each time that microprocessor-based unit 110 generates a trigger stimulus, a timer (e.g. clock circuit 154 of FIG. 4) is activated. If the patient or user does not activate the appropriate switch or control within a predetermined time interval, a digital signal is stored indicating a failure to respond. On the other hand, if the patient or user responds, a digital signal is stored indicating the user's reaction time (i.e. the time period between the occurrence of a trigger stimulus and the patient's reaction).

Since a series of delayed reaction tasks is used in each audio or visual delayed reaction test, the stored data that are accumulated during the diagnostic assessment will allow later analysis to determine various measures that relate to the patient's degree of attention. For example, measures that can be important include the user's fastest reaction time, his or her mean reaction time, and the standard deviation of reaction times. In addition, the difference between the results for audio and visual delayed reaction tasks may also be considered. For example, young children tend to respond more quickly to audio trigger stimuli than video trigger stimuli. Thus, the relationship between the results of audio and video delayed reaction tests for a patient may provide some insight as to that patient's relative deficit or development of both auditory and visual attention skills.

Figure 5:
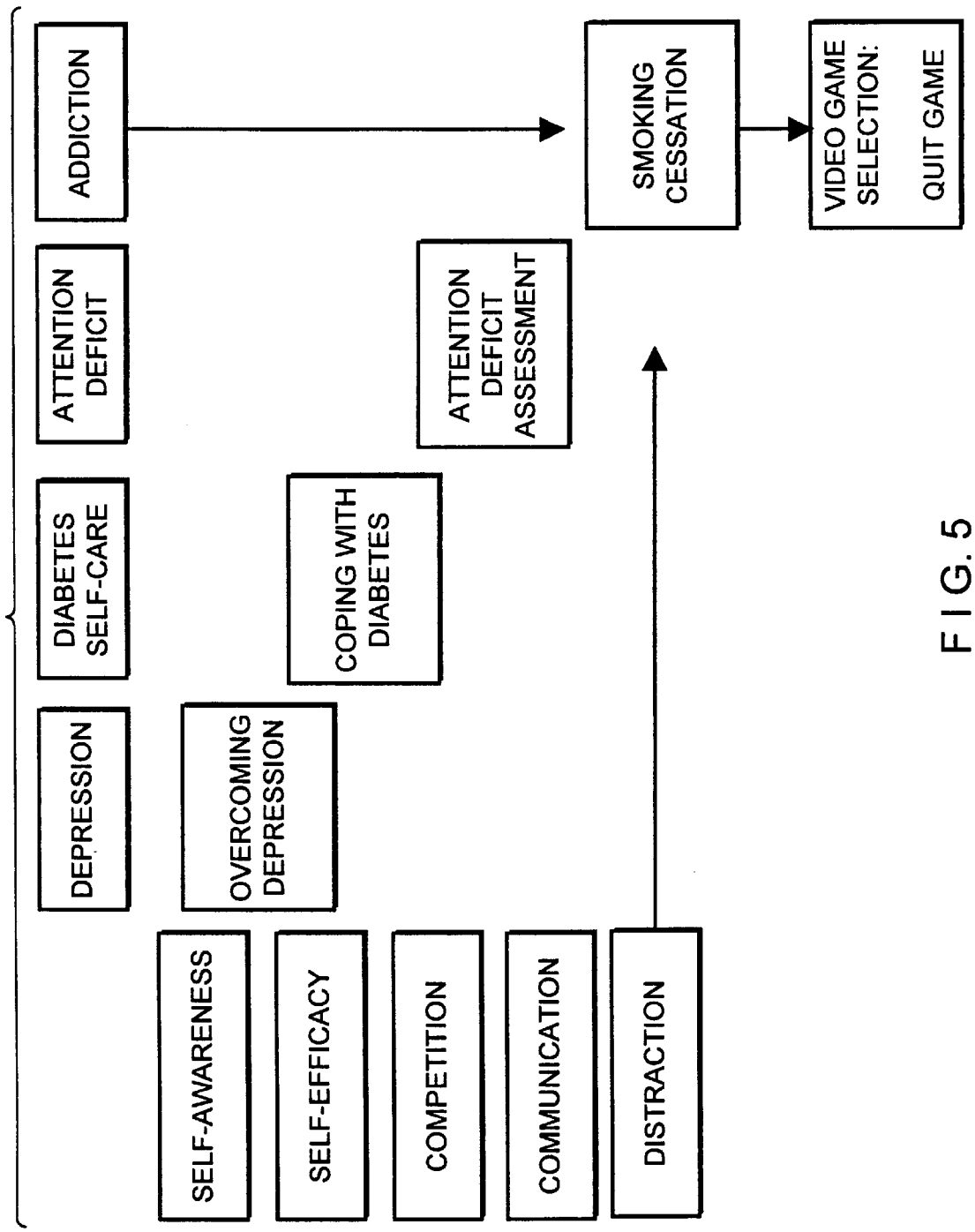
FIG. 5 is a flow chart illustrating how to select an appropriate video game treatment for some common medical conditions.

Aside from ADHD, in general, before using microprocessor-based unit 10 shown in FIG. 1, a patient will first visit a physician or health care professional to evaluate his or her medical condition. The physcian will diagnose the condition and choose the proper treatment based on patient needs. The flow chart in FIG. 5 shows the psychological strategies which the physician can select for treating depression, attention deficit, addiction and diabetes. The psychological strategies listed include self-awareness training, self-efficacy training, competition, communication and distraction. Other strategies well-known in the art, such as positive reinforcement, negative reinforcement, role-playing and the like can be employed as well. In addition to these, the psychological treatment strategy can include counseling methods and self-care instructions. Moreover, the treatment strategies can be combined as shown. For example, FIG. 5 shows overcoming depression is best ensured by a therapy which joins self-awareness training with learning self-efficacy to regain control over one's life. In the particular case highlighted with two arrows the medical condition to be treated is an addiction (such as smoking or alcoholism) and the appropriate psychological strategy for treating this condition is determined as distraction.

Once the psychological treatment strategy has been selected, the physician will choose an appropriate interactive video game program comprising this strategy. Examples of video games based on the most common psychological strategies will be given in the specific examples to follow. The program itself consists of electronically encoded instructions in data storage medium 20 (FIG. 1). The video game program is loaded from this medium 20 into microprocessor 12 and memory 18 of unit 10. This can be accomplished conveniently with a CD disk drive (not shown) since digital storage medium 20 is a CD disk.

The patient receives unit 10 prepared in this way and is instructed by the physician how and when to play the video game. The physician may also load several video games at once and instruct the patient when to play each one. Depending on the type of video game and the patient's capabilities, the physician will also determine what patient input device 16 should be employed in playing the game.

The patient takes home unit 10 prepared in this manner, and follows the prescribed treatment by playing the video game. Once in operation, unit 10 displays the graphical video game on display screen 14 and receives input through patient input device 16. The beneficial effect of playing the game is available to the patient at any time in his/her own environment.

A particularly convenient method for delivering a video game to the patient is shown in FIG. 2 Hand-held microprocessor unit 30 receives video games directly from hospital computer 52. The video game is transmitted through communication line 44 and received by remote communication unit 42. Unit 42 downloads the game directly into hand-held unit 30 via connection cable 40.

Hand-held unit 30 in FIG. 2 also communicates with clearing house 46 using communication line 44. As stated above, clearing house 46 can be a web server on the internet which is independent of the clinicians. The patient's progress in playing the video game can then be directly monitored by checking the video game scores. This information is screened, classified, and sorted by clearing house 46. An abstract or report is transmitted through transmission line 48 to facsimile machine 50 which can be conveniently located in the physician's office.

Unit 30 shown in FIG. 2 can also be used by the patient to check her medical condition. To do this the patient follows instructions embedded in the video game which tells her to connect to unit 30, the measuring device 54 (e.g. blood glucose meter in the case of a patient with diabetes). Unit 30 and device 54 may also be hooked up permanently by the physician. The video game instructions tell the patient that to continue playing she needs to perform a regular self-measurement using device 54.

For a patient with diabetes this involves checking her blood glucose level by drawing a small blood sample into device 54. The measurement data is then downloaded into hand-held unit 30 to be used as input for the interactive video game session. Exemplary video game using this technique to collect data is described in Example 4, below. Mean-while, the blood glucose-data is also passed through cable 40 to remote communication unit 42. From there the data follows the same path as described above for the video game score, and can be examined by the physician in the hospital.

The specific examples below describe exemplary microprocessor-based, interactive video games used for diagnosing and treating various medical conditions in human patients.

EXAMPLE 1

SMOKING

Figure 12A:
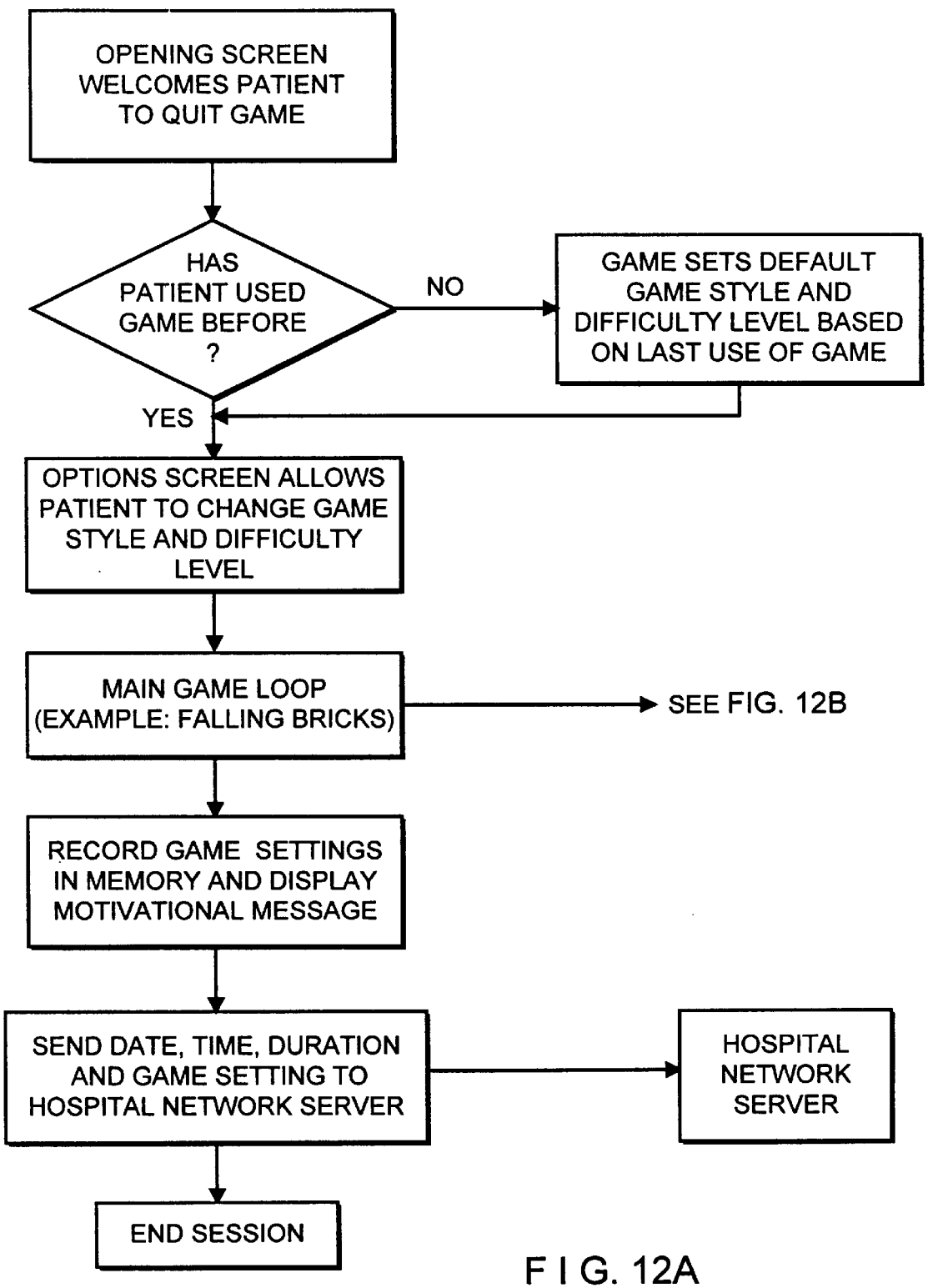
FIG. 12A is a general flowchart of an Addictiony/Distraction video game according to the present invention.
Figure 12B:
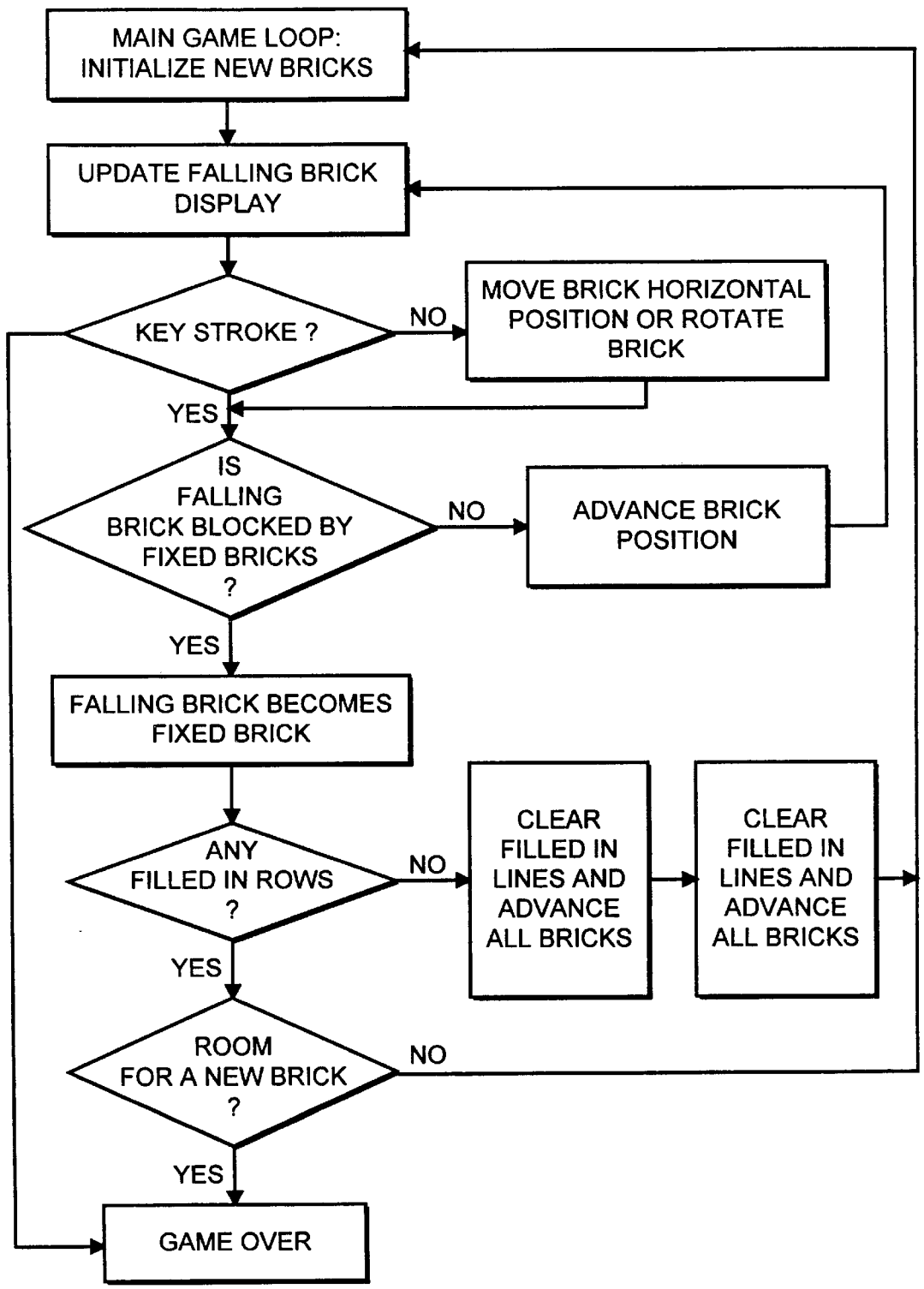
FIG. 12B is a detailed flowchart of the main game loop of the Addiction/Distraction video game shown in FIG. 12A.

The patient has a severe case of nicotine addiction. The physician determines, according to the flowchart in FIG. 5 that distraction is the best psychological strategy to induce the patient to quit smoking. Therefore, the physician prescribes playing the Quit Gamer a video game containing a behavioral program based on distraction. This game contains graphical game characters engaging in various competitive activities upon proper input from the user. The smoker plays the game whenever he or she feels the urge to smoke. An exemplary game to provide such an engaging distraction is shown in the flowchart illustrated in FIGS. 12A and 12B. In this example, the game is designed to distract the player with falling bricks which have to be arranged in rows.

During the game the main characters communicate to the patient instructions and simple strategies to quit smoking immediately and advise the user to take this approach, all within the context of an entertaining video game.

Alternatively, the game provides a timer and timeline for gradual reduction approaches to smoking cessation. Included among these programs are instructions for using nicotine patches. Built in notification will serve to remind smokers to shift to a lower dose patch. Once the smoker has quit, the video game will provide a coping/ relapse prevention model by using distract ion methods during periods of smoking urges.

A pilot study using the NINTENDO GAME BOY® as a tool to aid smoking cessation was highly successful. In the pilot project, seven smokers were give a Game Boy portable loaded with the Quit Game and instructed to use it any time they felt the urge to smoke. Six of the seven smokers successfully quit and were very enthusiastic about this approach.

An analogous video game strategy is followed in dealing with other substance abuse conditions, alcoholism, and obsessive compulsive disorders.

EXAMPLE 2

GROWTH DISORDER

The physician diagnoses the patient with a growth disorder, such as Turner's Syndrome or a similar condition, requiring growth hormone treatment and a psychological treatment strategy for helping the patient cope with his or her condition. By following a selection process similar to the one indicated in FIG. 5, the physician prescribes a video game combining self-awareness training, self-efficacy, role-playing, counseling and competition.

In the video game the graphical game character, Packy, is a young elephant who, like the patient, is on growth hormone therapy. The video game consists of three parts, each associated with a particular aspect of the treatment. In the first part Packy encounters obstacles which he must surmount, in the second he has to learn about growth hormone injections, and in the third one he has to keep a personal growth diary.

Figure 6:
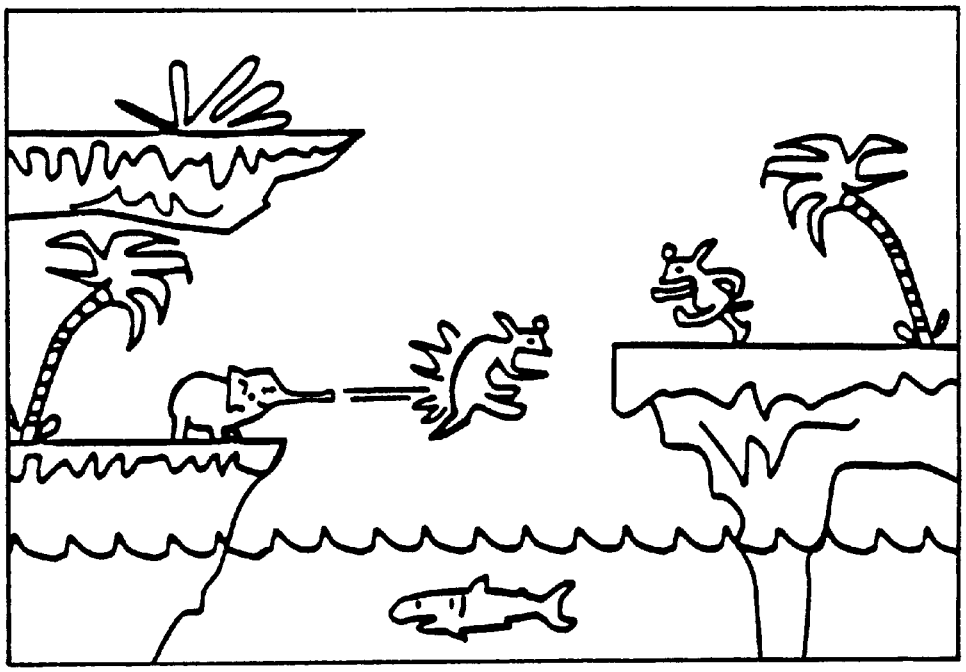
FIGS. 6 and 7 are exemplary screens of a video game for treating growth disorders.

In the first part Packy learns about things that grow, from the smallest things in the world to the largest ones, In each level of this part Packy can pick up icons of OM (representing a growth hormone shot) for a boost of energy. When he gets this boost, he will grow to a larger size until the energy wears or he gets hit by one of his opponents. Every time Packy meets someone who challenges him he must push them away by pressing a button to lower his head and walking into them, or squirt them by pressing another button. The small antagonists push and squirt away easily, but the large ones require some strategy such as combining pushing and squirting. This stage is depicted in FIG. 6. In each level Packy will occasionally find obstacles that require a growth shot to get past. He will also occasionally encounter a guardian to the pathway that asks him questions from the information learned in the other two parts, i.e. the growth hormone injection instructions and the personal growth diary.

Figure 7:
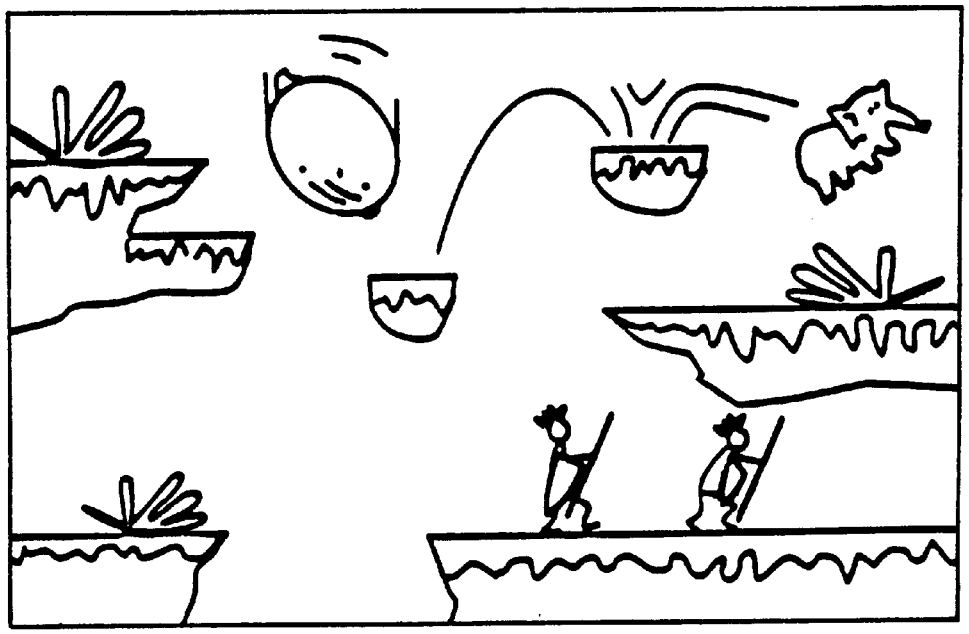

In another level of part one Packy has a dream in which he explores the world as a tiny creature. This scenario is illustrated in FIG. 7. He finds that he is very small himself, while all the surrounding items are very large. As he works his way to the end of this level he will encounter all types of animals and insects that are very small. This level will give Packy a feeling for what it is like to be really small. In the transition to the next level, Packy will wake up and see that he is still the same size, and grateful that he is not so small.

In the final level, Packy finds himself very large. He will be with the giant animals of the world. As he works his way through this level he will encounter all types of animals that are very large and the various types of obstacles they face in daily life. When Packy is bigger than the biggest elephant and cannot enter his home, he begins to realize the problems of being big.

Throughout his quest to feel comfortable with his growth Packy is accompanied by his mosquito sidekick Zippy. His companion plays the role of a mentor and counsellor throughout the various levels of Packy's adventures. In part two, the patient will learn about preparing and administering doses of growth hormone. First, the user will see how to mix a dose, then prepare a pen for injecting the hormone, and then actually see how an injection is performed. In the game aspect of this part the user will be challenged to mix and administer a dose seven times (Monday through Sunday) and provide accuracy results.

The third part of the game is a growth diary where the patient records and sees various graphics displaying his or her personal progress. Playing this game is reassuring and helps children overcome growth disorders by emphasizing self-awareness and self-efficacy training, role-playing, competition and counseling strategies embedded in the video game. Analogous video game strategy is also used to treat anxiety and hyperactivity disorders, various types of phobias, as well as enuresis. The flowchart for the Growth Game is provided in FIG. 13.

EXAMPLE 3

DIABETES

Figure 8:
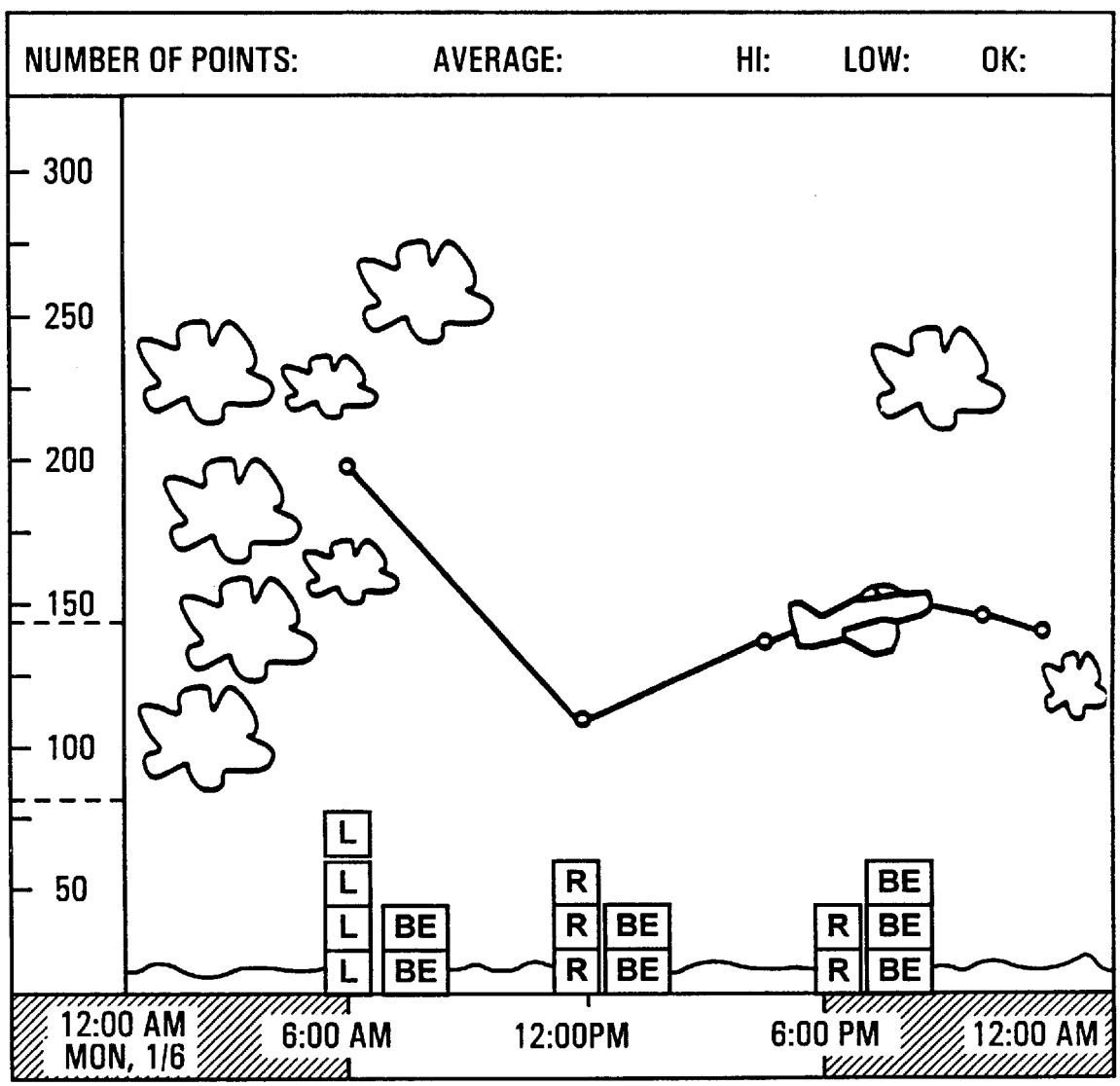
Figure 9:
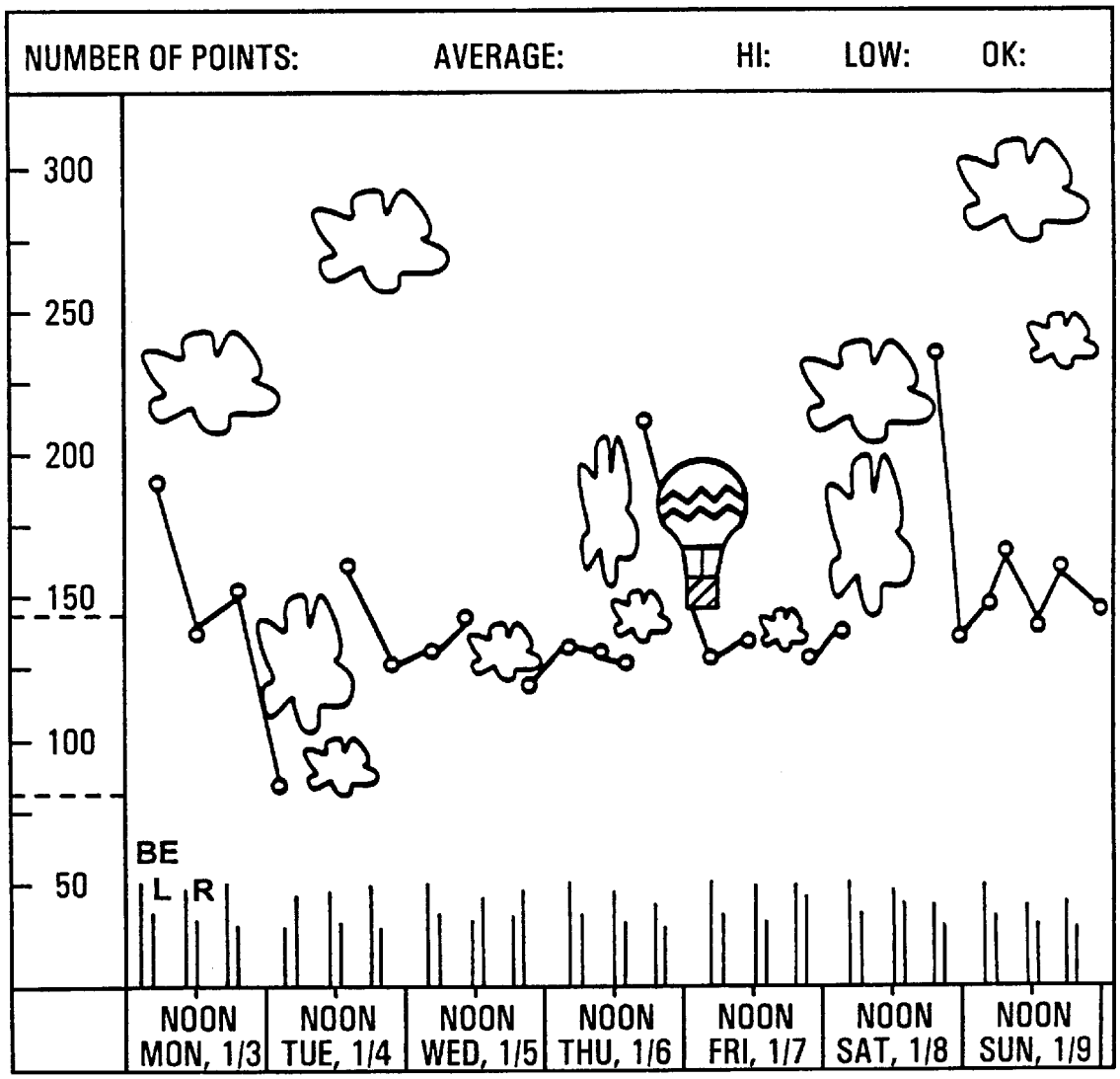

The patient is diagnosed with insulin-dependent diabetes. As treatment the physician prescribes insulin shots and a video game based on positive-reinforcement and self-management. In the video game the graphical game character is a pilot who has diabetes, just like the patient. The pilot needs to follow proper diet and exercise regimen to avoid crashing a plane or balloon which he is flying. The screens for the video game are shown in FIG. 8 and FIG. 9. Eating wrong foods causes blood glucose level to increase and the pain or balloon starts gaining altitude uncontrollably. Eventually, above a certain threshold, the balloon or the plane spins out of control.

Figure 11:
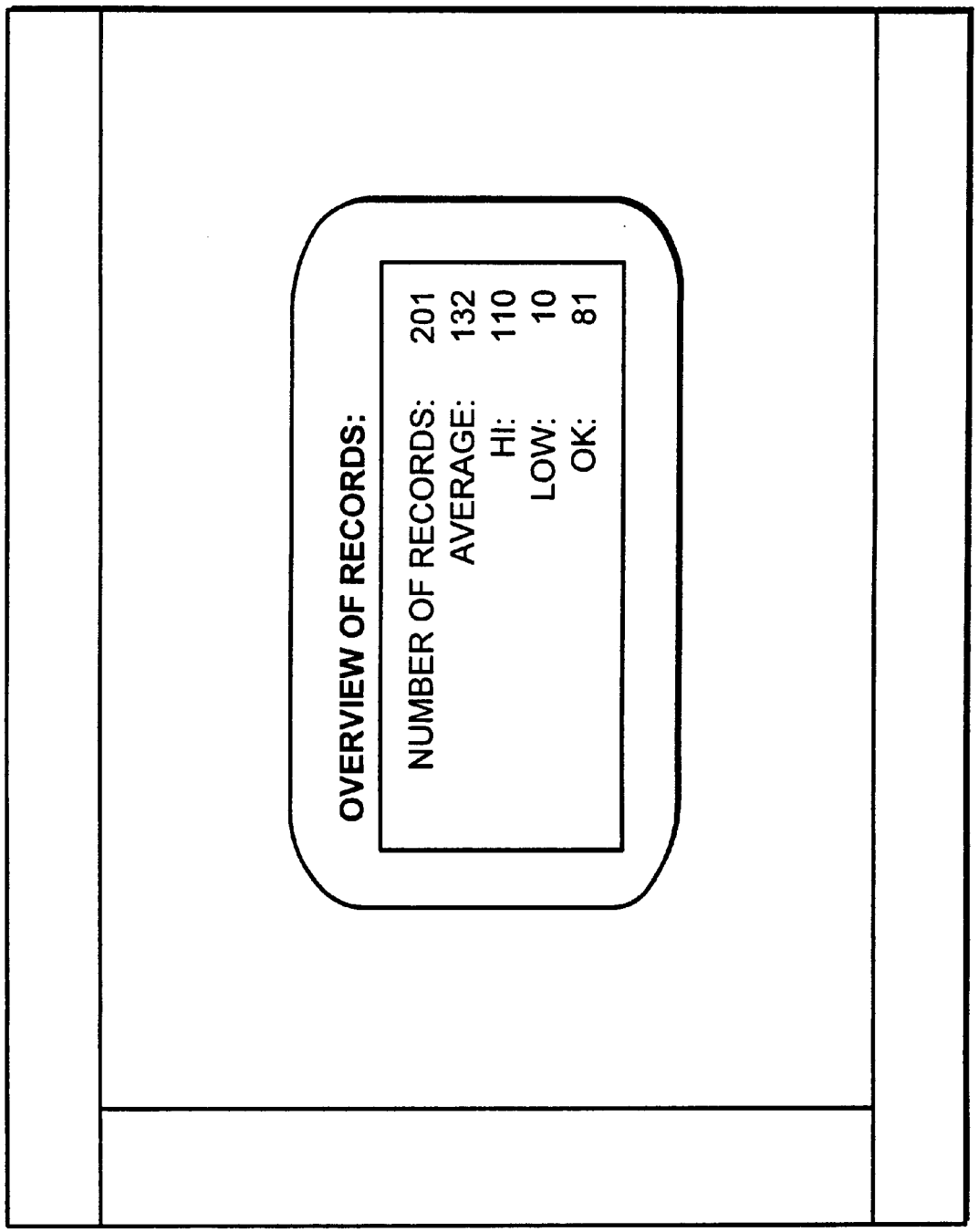
FIG. 11 is a screen indicating the blood glucose measurement results compiled for the video game of FIGS. 8–10.

During the game the patient is requested to enter his own blood glucose level by using blood glucose meter 54. An exemplary set-up for doing this is shown in FIG. 10. The reading is used in the game and can also be transmitted to the hospital, as described in example 3. Also, the user can view his blood glucose readings in the form transmitted to the hospital and used in the game. An example of such reading for a number of measurement records is illustrated in FIG. 11.

If the user does not comply with the request for measuring and entering his blood glucose level the plane or balloon disappears behind clouds, representing uncertainty in blood glucose level. This is visualized by the clouds in FIGS. 8 and 9. The clouds obscure the pilot's vision and lead to collisions with objects in the plane's or balloon's path. Alternatively, if the blood glucose level drops below a minimum threshold, the plane or balloon crashes against the ground.

This positive reinforcement-based strategy, in which the blood glucose level is correlated to a game parameter, e.g. plane altitude, teaches the patient how to cope with his condition on a day-to-day basis while making blood glucose monitoring fun. It also produces higher treatment compliance rates, especially in children who need to learn early on about proper diabetes self-management.

EXAMPLE 4

NON-INSULIN DEPENDENT DIABETES MANAGEMENT

A video game treatment can be used for management of noninsulin dependent cases of diabetes (NIDDM). In such cases the video game is an interactive information resource, as well as a role-playing game. The game helps the patient, especially an adult patient, explore the topic of Staged Diabetes Management. The information is presented in hypertext format, allowing the patient to select a stage, read a brief overview of it, and select details to examine it in greater depth in desired. The game encourages active involvement in learning and provides opportunities to rehearse various health behaviors and see the consequences that result by observing what happens to a graphical game character who displays these behaviors.

The content of the game is based on the Staged Diabetes management program, developed by the International Diabetes Center and Becton Dickinson & Company. The progressive set of stages ranges from least to most severe. For example, a patient in Stage I will learn to manage NIDDM through diet alone.

In the video game the user can configure the graphical game character in many ways. A checklist of choices allows the patient to combine a variety of physical features and clothes, as well as specifics about the character's health status including weight, age, and medications taken.

The game character, and thus the patient, will make decisions in realistic settings such as restaurants and parties where rich foods are available. Also, an exercise plan will fit in with the character's busy schedule of family, community, and work commitments. This format provides the patient with a playful atmosphere in which choices which the patient faces in his or her own life can be rehearsed.

If blood glucose levels do not remain in the normal range in Stage I, the patient is instructed by the graphical game character to advance to the next treatment steps, eventually arriving at the stage where the patient will be instructed to inject insulin to control blood glucose levels. The goal of the NIDDM game is to remain at Stage I.

Similar video games can help to deal with hemophilia, and other medical condition requiring the patient to be aware of his or her surroundings.

EXAMPLE 5

ASTHMA

A youngster diagnosed with asthma is given an asthma self-management game for hand-held unit 30. The graphical game character, a young dinosaur from the pre-historic town of San Saurian, must cope with and manage his asthma. The game character confronts common asthma triggers, while learning to recognize early warning signs of an oncoming asthmatic episode. Asthma management techniques including avoidance, relaxation, and medicinal inhalers are part of the daily routine for the young dinosaur who must return to his cave. The dinosaur runs, jumps and shoots a squirt gun at oncoming triggers while conquering each level and mastering his condition. In addition to these inputs, the dinosaur requests the player to input the player's asthma condition by using physical parameter measuring device 54, which in this case is a respiratory flow meter. These data can then be transmitted to the physician as described above.

Playing the video game involving these real asthma triggers, relaxation techniques, etc., affects the mental state of the player to improve his own asthma management outside of video game sessions. This treatment based on role-playing and positive reinforcement makes the patient aware of the importance of prescribed drugs and teaches appropriate measures for dealing with the patient's condition in real life situations.

EXAMPLE 6

EATING DISORDER

The physician determines that the patient suffers from an eating disorder causing the patient to gorge. The physician loads into the patient's microprocessor-based unit 10 or hand-held unit 30 a video game in which the graphical game character has to stay thin to survive. The game challenges confronting the game character include avoiding fatty foods to stay trim and eating a sufficient amount to combat dragons and surmount obstacles on his way. Doing this involves making choices about what food presented on the screen to eat, keep for later, or reject. wrong food choices have diet consequences in the graphical character's ability to survive. The game is scored according to the length of time the patient is capable of keeping his game character alive and obstacles the character overcomes.

The physician instructs the patient to play the game every time the patient feels an eating urge outside regular meal times. During a regular follow-up visit the doctor evaluates the patient's progress and checks the scores obtained in playing the video game. Based on the analysis of the sores the physician determines the severity of the problem and gets an insight into the patient's motivation to comply with the therapy.

Sufficiently high scores reflect progress and readiness to proceed with the next treatment stage. At this point the physician may instruct the patient to play another video game designed for milder eating disorders or a game utilizing a different psychological approach, e.g. negative reinforcement or distraction.

EXAMPLE 7

DEPRESSION

A psychiatrist enrolls a patient in a series of home-based interactive video game sessions which the patient accesses from his microprocessor-based unit 10 through hospital network 26. The video game is then transmitted from the hospital network server 28 to the patient in unit 10. The game involves interaction with a graphical game character resembling the Yoda character from the popular movie "Star Wars". Yoda acts as a counselor and mentor to the patient, preparing him for various trial episodes in the video game. Based on patient's scores in playing the video game sent, the physician reviews how the patient responds to video game counseling and prepares another game to be transmitted to the patient. This treatment method is part of an on-going therapy for mild to medium-severe depression. This approach is also used for schizophrenia and other purely psychological disorders.

EXAMPLE 8

ATTENTION DEFICIT HYPERACTIVITY DISORDER

The prototype video game for ADHD was developed and tested with an assessment battery for the SUPER NINTENDO™ system for use with children between ages 6 to 12. Research with children in this target group indicated that the prototype is appealing and motivating and can assess varying levels of proficiency in attentional tasks of continuous performance and delayed response.

A home-based, highly motivating game that includes continuous performance tasks as described herein, can serve two important management functions for children with ADHD, both of which are currently unavailable. First, it gives these children opportunities to practice tasks requiring sustained attention and receive performance feedback within an educational video game designed to improve their knowledge and attitudes about ADHD. Second, it provides a home- or school-based continuous performance task that would have great value as an additional, objective outcome measure in double-blind trials of medication for ADHD.

Following the video game development, an interactive multimedia intervention protocol for ADHD, based on the prototype, was completed. The intervention has two components—(1) a video game that offers experiential education about focusing attention and controlling impulsiveness, which was evaluated in a controlled, six-month outcome study with 80 ADHD patients ages 6 to 12, and (2) a multimodal assessment too, for medication management, which was evaluated in home- and school-based, double-blind medication trials with 30 or more children who have ADHD.

The experiential education game provides, in an action-oriented simulation, opportunities to practice focus of attention and control of impulses, supportive and educational performance feedback and general information about ADHD and its treatment. The medication management system will allow patients to use a NINTENDO™-delivered battery of continuous performance tasks and then send the results via modem from home to a central computer that will enable communication of data directly from the child's home to the physician. Parents and teachers will respond to behavior rating scales via the NINTENDO™ and modem so that multimodal assessment can be accomplished conveniently and at low cost on a daily basis.

The situation-dependent nature of ADHD indicates the need for a comprehensive test, as an attention deficiency is not always apparent in a clinical environment. The ADHD intervention allows for a multilateral approach. Data will be collected from parents and teachers through the use of questionnaires they can answer on the NINTENDOT™ system.

Data from the children will include their test results in the NINTENDO™-based battery of Continuous Performance Tasks (CPT battery). The system coordinating this approach will include the data collection system (electronic questionnaires and CPT battery results), a modem that will send the data from the NINTENDO™ to a central EBM computer via telephone lines, and a data analysis system with statistical tools that can generate clinical reports about individual patients and can aggregate data about many ADHD patients for use in epidemiological research.

The medication management system which can comprise an intervention cartridge, a modem and an IBM™-based reporting system will be available to health care providers and researchers. The ADHD intervention as a standalone game cartridge will be marketed to the public, especially for children with ADHD and their families. While the NINTENDO™ system and the IBM™ Microsoft™-based language have been identified as exemplary modes of practicing the present invention, it will be understood by those skilled in the art, that a plethora of other microprocessor-based systems and computer codes are available with equal adaptability.

Computer hardware is available to an ever increasing percentage of U.S. homes and a growing number of adults are playing video games regularly. ADHD intervention has the potential to reach a significant number of adult patients There is ample research evidence showing that educational multimedia can provide powerful learning environments for adults. Several research studies have synthesized the results of controlled trials and have found positive effects of multimedia on adult learning and that learning with multimedia is as effective for adults as it is for children and teenagers.

Deardorff, W., *H. Educ. Ouat.*, 13:61–72 (1986); Kozma, R., *Rev. of Educ. Res.*, 61:179–211 (1991); Zahner et al., *Educ. Tech. Res. & Dev.*, 40:55–62 (1992).

The studies find that adults learn more efficiently with well-designed multimedia than with print, video, or traditional classroom teaching; generally enjoy learning with multimedia more than with other materials and methods; and increase their motivation to learn about the topic when they use multimedia that meets their instructional and informational needs. These findings are identical to those in studies with younger people. The ADHD intervention according to the present invention and as outlined below, will appeal to a wide audience of adolescents and adults, even though the game will be targeted to ages 6 to 12.

Initially, the following was developed—(1) a battery of auditory and visual tests of attention (called MAB for Microcomputer Attention Battery), which run on a standard SUPER NINTENDO™ system, (2) an administrator program for an IBM compatible computer which configures the attention tests and allows the data to be stored on the computer's hard drive, and (3) a hardware device linking the computer with the SUPER NINTENDO™. MAB includes both auditory and visual Delayed Reaction time Tasks (DRT's) and both auditory and visual, performance-paced, continuous performance tasks (CPT's) which are presented with and without distractions.

Microcomputer Attention Battery (MAB) is composed of two separate programs running on two connected platforms. The actual test battery (as presented to the test subjects) runs on a Super Nintendo Entertainment System™ (SNF-S), and receives test parameters from and communicates test results to a test administrator program running on an IBM™ PC or compatible computer. Communication between the two platforms is accomplished through a custom SNES-to-RS232 hardware device.

The test provides auditory and visual delayed reaction time tasks (DRT's) and auditory and visual performance-paced continuous performance tasks (CPT's). This test battery allows the researcher to configure the tests to suit the particular research goal.

The Administrator Program controls the test process, collects test data from the SNES, and places test results in a database. It contains summary features that break down the database by grade for normalization. It also has the ability to save test and demonstration configurations for immediate and consistent set-up of each trial. The demonstration is a very brief trial covering all the tests before the subject is asked to complete the actual test battery. This helps minimize learning curve effects. Distortion from the test-retest effect is greatly reduced, since the demonstration is done consistently with all subjects.

In the visual continuous performance task, for example, the child watches the screen as a car drives past mountain scenery and a line of trees. Each tree has fruit in it, either grapes, apple, orange, or lemon, one of which is the target fruit and is designated as the signal. The child is instructed to press the response button each time the car passes the target fruit. When the button is pressed, a net reaches up from the car to grab the fruit with appropriate sound effects. If the fruit is a correct target fruit, the car speeds up as evidenced by a shorter interstimulus interval (ISI) between trees and an increase in the pitch of the car engine sound. Missing the target fruit, or impulsively pressing on a non-target fruit, will slow the ISI and lower the engine sound, thereby slowing the car. If the child presses the button after the fruit has passed the car, but while it is still on the screen, it is defined as a late hit and the ISI and engine speed are not adjusted. In this way, a miss due to reaction time alone will not be recorded as a miss and the speed will remain constant. During the distraction phase of the visual continuous performance task, butterflies, birds, flying saucers, and frogs are also moving on the screen to distract the child from the target stimuli.

In the auditory continuous performance task, the car is driving past the trees at night with headlights that illuminate the tree trunks, but incompletely illuminate the fruit in the trees. The child must listen for either a high pitched beep (indicating a target) or a low pitched beep (indicating a non-target) and respond accordingly. The speed of the trees and the auditory clues from the net and the engine speed continue to reinforce the child on correct hits. During the distraction phase of the auditory continuous performance task, a digitized voice of a child randomly says "Press it," "Now," and "Go" to distract the child from the correct beeps.

The result of each DRT is sent to the administrator program, which calculates the minimum, mean, standard deviation and number of false starts. The four phases of the CPT's (visual or auditory, undistracted or distracted) are calculated separately. Thirty-two evenly spaced samples of the ISI are taken during each phase. These are then averaged for each test, or can be displayed graphically. The administrator program also records the number of targets missed, the number of impulsive hits, and the number of late hits.

These studies were conducted with groups children such a as a Normal Sample of twenty-three children (13 boys and 10 girls) who were recruited from an after-school program to take the test after parents had been notified of the study and given an opportunity to withdraw their child from consideration. Children were selected from among volunteers on a first-come first-serve basis to attempt to fill a matrix with two slots for boys and two for girls at each age from 5 to 12.

The procedure involved each child taking the test seated comfortably in front of a viewing screen. The test was administered by a school nurse who recorded observations of the child's test behavior. Prior to taking the test, a demonstration test was given using six test modules and two instruction screens. Standard directions were given and the child was given an opportunity to ask questions. When the child clearly understood the test and had no questions, the actual test was given. After the test, each child was asked a number of questions including how well they liked the test and how often they played video-games.

In all, 24 children completed the questionnaire after completing in the after-school programs. They were asked how well they liked the game, whether the game was fun and whether it was interesting. In response half the children answered that they liked it a lot, five liked it a little, and seven were in the middle. None expressed dislike. Sixteen said it was very fun, 7 said somewhat fun and only one was in the middle. None expressed that it was not fun to any degree. Half the children said very interesting, seven said somewhat, three were in the middle, and one each said not very or not at all.

Outcome measures were entered into a forced-entry multiple regression with prior experience with video-games, gender, and age as factors. Three of the fourteen outcome variables showed a statistical relationship (all at the $p<0.05$ level) to prior videogame experience. These were mean auditory reaction time and the variability of both visual and auditory reaction time. However, only one of these (the variability of visual reaction time measures) varied in a direction that indicated that prior experience was helpful. The other two showed a slight performance decrement with prior experience.

Only one outcome measure showed any statistical relationship with gender, mean visual reaction time, which showed a slight advantage for boys at the p<0.05 level. Age was related to all the reaction time variables except the variability of the auditory reaction time, and all of these relationships were strong, at the p<0.005 or p<0.001 level, and in the expected direction. The only CPT variables that showed a relationship with age were the two measuring mean interstimulus interval in the auditory distracted and undistracted phase (p<0.05). This was in the expected direction with older children performing better.

These data indicate that MAB is a very appealing test to children. Most children described it as fun and it was clearly seen as a game and not a test. This high interest is necessary if a test is to be incorporated into an experiential education game. In addition it should help assure that the test measures differences in the ability to focus attention and not simply differences in motivation. On the other hand, this may work against the diagnostic potential of the test. If ADHD involves a deficit in motivation-related factors, this high interest could wash out differences between children with and without ADHD and a boring test may have greater discrimination.

Medication Study

Children were selected for study if they had been diagnosed with ADHD by their own physician and were taking shortacting, stimulant medication, either methylphenidate or dextroamphetamine. Fourteen children were enrolled in the study. The ages ranged from 5 to 14 (average=9.9 years).

To avoid confounding a medication effect with a practice effect, children were assigned at random to one of two groups with Group one tested initially between 8 a.m. and 8.30 a.m. before they had taken their medication; and then again two hours later. Both methylphenidate and dexedrine have peak effects around two hours after ingestion. Group two was tested initially at midmorning, approximately two hours after taking their medication and then again 2.5 to 3 hours later. Both medications would have substantially lost effectiveness by this time for most children.

Results were analyzed with a repeated measures procedure using medication status (on or off) as a within subject variable, and order (on-med-first or off-med-first) as a between subject variable. The off-med-first group had eight children ranging from 5 years to 13 years with an average age of 9.5 years. The on-med-first group had 6 children ranging from 9 years to 14 years with an average age of 10.5 years.

This medication study was designed to tease apart a potential practice effect (doing better on the second try regardless of medication condition) from a medication effect (doing better while on medication regardless of test order). If there is a main effect of medication, then children do better on medication than off regardless of whether the first or the second test was done while on medication. If there is a main effect of group, then children who were tested on medication first are different from children who were tested off medication first. The most likely cause of a group effect is a non-random division of the subjects into the med-first and the no-med first groups. Finally, if there is a practice effect, this will show up as an interaction between group and medication. Children in the medication first group will do better off of medication (their second test) while children in the no-medication first group will do better on medication (their second trial).

Several variables, and combinations of variables, show a strong medication effect. The variability of performance during the visual reaction time test (SDVRT) showed a significant main effect of medication. This effect was strengthened when all four reaction time measures were considered together in a multivariate analysis. There were no significant practice effects seen on these variables.

The eight children in Group one of study two were compared to the normal sample in their performance the first time they took the MAB. Because they took the test first, before taking their morning medication, their medication status does not affect this comparison. These eight children differ from the normal group in that they had been diagnosed with ADHD and were being treated with stimulant medication. Results of all fourteen variables are analyzed with an analysis of variance procedure, controlling for age.

The average age of the eight children with ADHD was 9.5 years compared to 7.9 years for the children in the normal sample. This is not a significant difference. Results for the reaction time variables were invalid in four of the ADHD children because of a technical error, leaving only four children. These four children were significantly different from the normal sample on three of four of the reaction time measures, highly so for two measures of mean reaction time.

Strong statistical differences are seen between the reaction times of the four valid ADHD children and the normals, and mildly significant differences are seen in the measures of variability during the CPT's when they are considered together. In all but one of the variables, the group mean of the ADHD children indicated worse performance than the group mean of the normals. These differences cannot be accounted for by age, which was controlled in the statistical analysis, but other explaining factors cannot be ruled out. There is not sufficient data to determine a cutoff score that would distinguish between normal and ADHD. The strongest statements can be made about the acceptability of MAB to a wide range of children and about the medication effect, where children served as their own controls.

MAB provides a feasible attention battery for use with children. The hardware and software combine to produce a flexible presentation of the attention tasks in an inexpensive and familiar SUPER NINTENDO™ format which was configured to vary the parameters of the task. The data were successfully and conveniently stored on the hard drive of the computer.

Children of all ages from 5 to 12 tolerated the 25-minute task very well. A few even commented that they would rent the game, if it were available in the video stores, to try to get their speed faster. It is possible that high motivation factors will make less able to discriminate ADHD from normal (especially if ADHD involves motivation-related factors as speculated by some). It is also possible that attention differences will remain even with high motivation. If this is the case, a high motivation form would be preferable as it would reduce differences due to effort, which are not related to ADHD. MAB provides a way to explore this theoretical question.

MAB does not appear to be biased toward boys or toward children with extensive video game experience. Despite the prevalence of video games in the general population, we still ran into children with minimal experience. Because of this, it is important to minimize the effect of prior video game experience, and MAB appears to do this.

The lack of an age factor across the range of 5 to 12 is puzzling, as children would be expected to improve on attention tasks over this period. Developmental changes were seen in the reaction time outcome measures of MAB, but not in the CPT measures. Although comparisons between children who reportedly have been diagnosed with ADHD and normals suggest that NAB may be able to discriminate ADHD children from normals, small numbers limit the conclusions that can be drawn from this comparison.

ADHD Intervention

The ADHD intervention has two components—(1) an educational game and (2) a medication management system. The following is a description of the game and the medication management system.

The ADHD video game delivers experiential education by providing opportunities for children to practice their attentional skills. It is targeted in terms of themes, characters, reading level, and difficulty of game play-to children ages 6 to 12. Children who play the game will engage in continuous performance tasks (CPT's), rehearse attentional skills during game play and learn about ADHD, all in the framework of a simulation game.

In the ADHD video game children play the role of a rabbit, or two rabbits in two-player mode, all of whom have ADHD. They will be challenged to reach a destination quickly. For example, they may have to save someone before time runs out or, they may have to go somewhere, find something of value, and bring it back fast. These types of scenarios can be used in a game strategy that requires speed and accuracy, skills that ADHD children typically need to practice because attentional focus and concentration are required. The game alternates between (1) CPT's, where the rabbit is in a vehicle, and (2) side-scrolling, action video games where the rabbit is on foot and still trying to reach the destination. The CPT's involve a vehicle-car, boat, and then space ship-the same way the prototype used a car racing along a road while the player was asked to press a button to grab targets.

When the software starts up, it gives the player two options—(1) Races or (2) Game. The races are the CPT's and DRT's. The player goes through six in a row and receives a score on each one. The Races are used for fun or can be assigned under the supervision of a clinician for assessment, or during double-blind medication trials. The tasks are:

1. Visual Delayed Reaction Time Task
2. Auditory Delayed Reaction Time Task
3. Visual Continuous Performance Task
4. Visual Continuous Performance Task with visual distractions
5. Auditory Continuous Performance Task
6. Auditory Continuous Performance Task with auditory distractions The game will continue until 12 CPT's and 12 game levels are completed, and the game levels will increase in difficulty. This will allow the six CPT's each to be repeated twice. It will also make the game long and challenging enough to maintain children's interest for many sessions. It is typical for children to spend 40 to 60 hours, over several months playing a challenging NINTENDO™ game until they can complete every level. Each game level will require skills that were rehearsed in the previous CPT or DRT. Players will receive individualized feedback about their skill in the game on these tasks. Feedback will refer to their previous performance in the CPT or DRT. Players will receive bonus points for successfully accomplishing the CPT and DRT tasks within the game levels.

Throughout the game levels, players must look for an icon, for example a red rose, which provides information about ADHD. The information deals with symptoms, medication, behavior management, environmental accommodations, social skills, and family and peer relationships. When more than one child plays the game, each controlling the actions of a rabbit, they will soon realize that it is advantageous to cooperate. The rabbits will gain the most points if they wait their turn, stay close together (which requires at least one child to pay attention to the location of their partner's rabbit), and give each other what they need (supplies, food, jewels etc.) so both of them can have peak strength and power to meet oncoming challenges.

The video game will improve the self-concepts and self-esteem of children with ADHD; improve attitudes about ADHD and increase their motivation to learn more about it; enhance children's willingness to talk about ADHD with friends, family and clinicians; increase children's knowledge about ADHD; teach children some of the skills needed to focus attention and control impulsivity; and contribute to a decrease in behavioral problems at home and at school.

Medication Management System

The ADHD intervention provides the option to play the Races only. The Races are CPT's and DRT's presented in an appealing and motivating format that children enjoy. To conduct double-blind medication trials, a clinician supplies an ADHD patient with a SUPER NINTENDO™ system with modem and a cartridge containing the ADHD intervention.

Double-blind medication trials can occur daily, at home, with data transmitted via modem to a central computer. Patients send their daily data via a telephone link, and the central computer collects, analyzes and reports the data. Patients send their data via modem, while parents complete on-line rating scales and teachers fill out paper versions of rating scales. These data are compiled and a report sent to physicians as soon as the patient's double-blind trials are completed.

The medication management system supports a multilateral approach to medication management. The system provides a convenient way for parents to respond to rating scales and for patients to take a computer-based assessment battery with results sent electronically to clinicians. The system reduces the time and clinical costs involved in double-blind trials, and provides a method for administering double-blind trials and a powerful tool for epidemiological researchers to analyze aggregate data collected from ADHD patients.

Stimulant medication has been repeatedly demonstrated to have a beneficial short-term effect on the core symptoms of ADHD. However, choosing the proper dose and differentiating real therapeutic effects from expectation and placebo effects is not easily done with known methods. Double-blind trials of medication efficacy, as presented by this invention, help prove that the observed benefits go beyond a placebo effect, document the most appropriate dose, and monitor for side-effects at different doses.

The medication monitoring mode of the ADHD intervention is designed to assist in the daily home measurement of medication effects, including a behavioral rating scale, a side-effects scale, and a continuous performance test, and to transmit this to the clinician on a daily basis for analysis.

For convenience, double-blind medication studies are often done by changing the dose of medication on a weekly basis. Unfortunately, gradual improvement or deterioration in the child's behavior over the course of the trial will be confounded with a medication effect in this model. In addition, expectations can center around the dose for the week which can affect the results. Parents and teachers may not know what dose is taken in a given week, but expectations can form around the weekly behavior, knowing that the same dose is given all week. Because both methylphenidate and dextroamphetamine have a very short time course, it is possible to vary the dose on a daily basis and therefore eliminate these confounding factors. However, this makes it difficult to include a performance task as an outcome measure unless the child is brought to the clinic every day, or the trial is conducted in the hospital or other controlled environment. The medication monitoring phase of the ADHD intervention makes it cost effective to gather performance data at home on a daily basis and transmit this data to the clinician.

The ADHD intervention continuous performance tasks are completed each day of the trial as follows. The child's family is given a SUPER NINTENDO™ system, a suitable modem, and a cartridge with the ADHD intervention and instructed on their use. They are asked to have the child do the assessment mode of the ADHD intervention (the Races) once each day, two hours after a dose of medication. On school days, this is around 6 p.m., which will be two hours after a 4 p.m. dose unless arrangements can be made to use the ADHD intervention at school. Once each evening, the parent completes the 10-item Rating Scale and a side-effects questionnaire using the ADHD intervention, and sends the daily scores over the telephone to the researcher. The ADHD intervention will automate the process of sending the scores over the telephone by dialing the telephone number automatically and sending the data to the central computer once a phone connection has been made. The teacher will be asked to fill out and send in a Rating Scale and a side-effects rating scale on paper at the end of each day.

For each subject, daily differences in all outcome measures are visually displayed and analyzed with a repeated measures statistic. Results from all trials are statistically analyzed to determine the degree to which ADHD intervention scores differ from behavioral rating scores and the effects of age and gender.

Following all double-blind medication trials, the attending physicians reviewed the reports, and identified the benefits and drawbacks of this method of reporting. Children and their parents were also interviewed. All data on the intervention were used to revise the medication management system before it was made into the commercial product.

Figure 14:
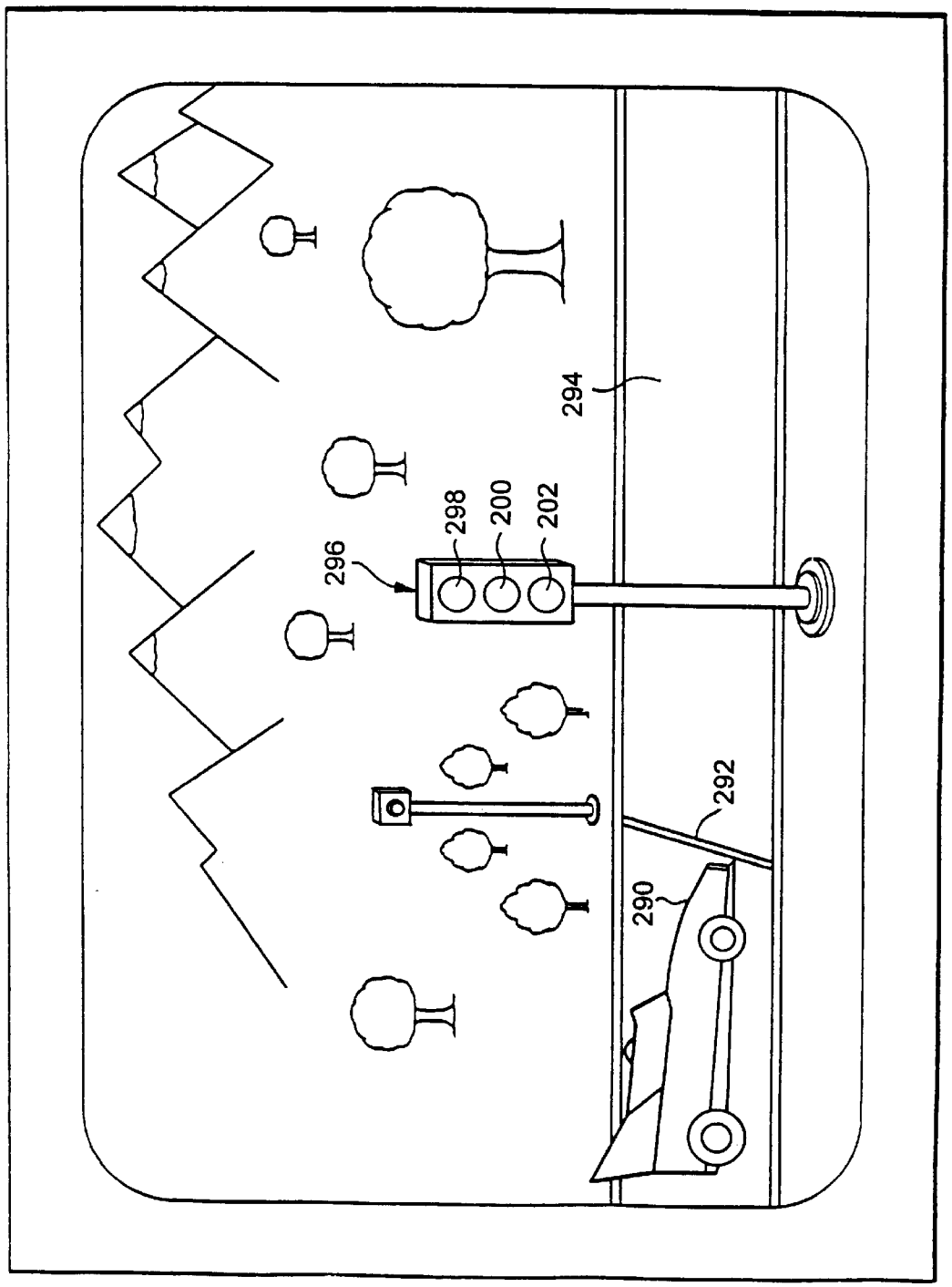
FIG. 14 illustrates a graphic display suitable for use when a microprocessor-based patient unit administers a delayed reaction test in an embodiment of the invention that is configured for diagnostic measurements relating to Attention Deficit Hyperactivity Disorder (ADHD).

FIG. 14 shows an exemplary screen display for the ADHD video game. A car 290 is positioned at a starting line 292 on a roadway or racetrack 294. A traffic signal 296, having a red light 298, an amber light 200, and a green light 202, is prominently displayed. As each visual delayed reaction task is generated, micro-processor-based unit 110 (FIG. 3) causes sequential illumination of red light 198, amber light 200, and green light 202. Amber light 200 serves as the warning stimulus, with green light 202 providing a trigger stimulus after a randomly generated time delay that is within the time delay range that was established when the visual delayed reaction test being executed was established by the clinician or the administrator having control over the diagnostic testing.

During the audio delayed reaction tests, the three lights of traffic light 200 in FIG. 14 are extinguished and program instructions that are stored in external memory unit 112 (FIG. 3) result in generation of suitable audio warning and trigger stimuli by sound generator 162 of FIG. 4.

In arrangements having sufficient memory and sound generation capability, the words "ready . . . set . . . go" are used with the time interval between "set" and "go" being a random value within the range of values selected when a clinician established the diagnostic procedure. Two tones that are clearly distinct from one another also can be used for the warning and trigger stimuli. The currently preferred realizations of embodiments of the invention that are directed to diagnostic assessment of ADHD provide for both visual and audible continuous performance tests. In each test a sequence or series of events occurs for which the patient or user is to respond by activating a predetermined switch or control such as the control switches 144 in the arrangement of FIG. 4.

The continuous performance test used in the currently preferred embodiments of the invention are performance-paced in that the interstimulus stimulus interval (i.e. the time that elapses between consecutive stimuli) is reduced by a predetermined amount each time a correct response is made and is increased by the same or a different predetermined amount if an improper response occurs (i.e. the user responds to a non-target stimulus or fails to respond to a target stimulus).

Figure 15:
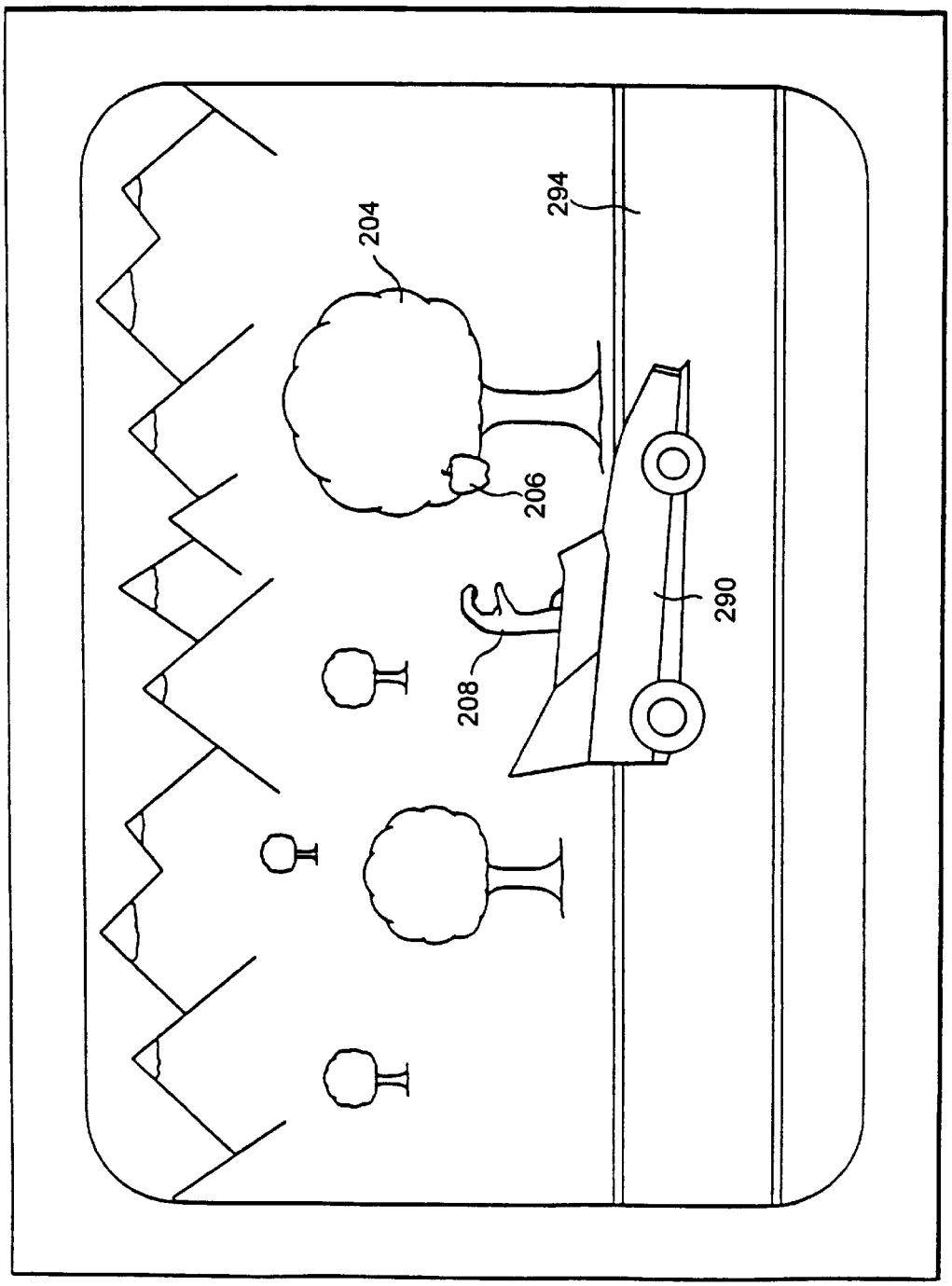
FIG. 15 illustrates a graphic display suitable for use when a microprocessor-based patient unit administers continuous performance tests for diagnostic measurement relating to ADHD.

The video display for the continuous performance tests of the currently preferred embodiments is indicated in FIG. 15. In FIG. 15, the car 290 that is used in the above-discussed delayed reaction tests is shown traveling along a roadway 294. Periodically, the car 290 approaches a tree 204, which is positioned along side roadway 294. As car 290 approaches a tree 204, various types of fruit (oranges, apples, lemons and grapes) will appear, hanging downwardly from a branch of the tree. The object is for the patient or user to respond to a specified type of fruit only (e.g. apple 206 in FIG. 15) by depressing a selected switch such as one of the switches of control switches 144 in FIG. 4. When the appropriate switch is pressed, a hand and arm extend upwardly from car 290 to capture the fruit. As previously noted, with each correct response, the interstimulus interval is decreased (i.e. car 290 appears to travel at a higher rate of speed) and with each incorrect response or failure to respond, the interstimulus interval is increased (car 290 appears to travel slower).

In the audio continuous performance tests of the referenced realizations of the invention, the display shows car 290 traveling at night, with only a portion of roadway 294 being illuminated by the car's headlights. Each time the car approaches a darkened tree 204, a low-frequency radar-like "beep" is heard if the tree does not bear is present, the desired fruit (apple 206 in FIG. 15). When the proper fruit a high-pitched radar-like beep is emitted.

Figure 16:
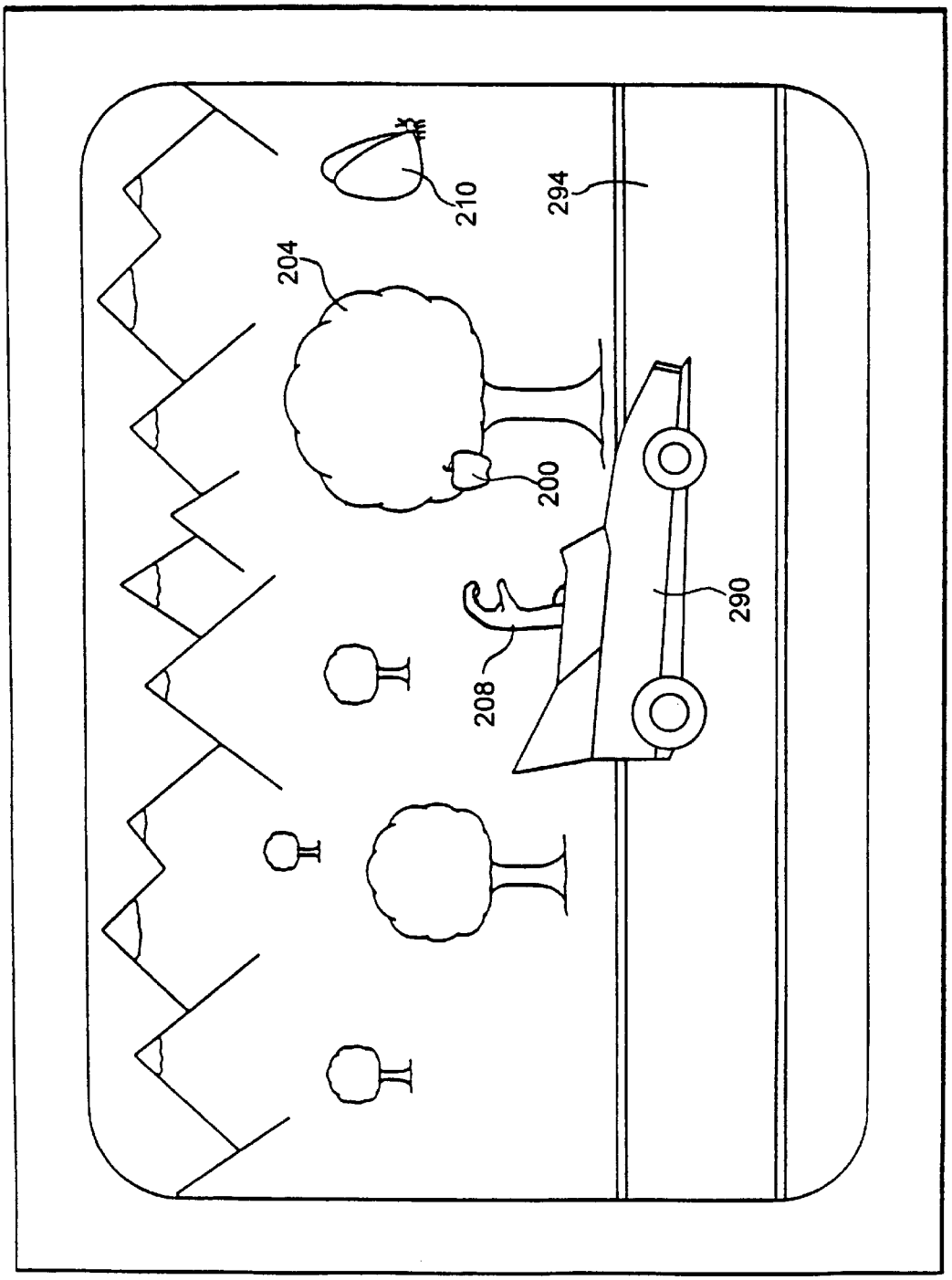
FIG. 16 illustrates a graphic display suitable for use when a microprocessor-based patient unit administers continuous performance tests that also include visual distractions for diagnostic measurements for ADHD.
Figure 17:
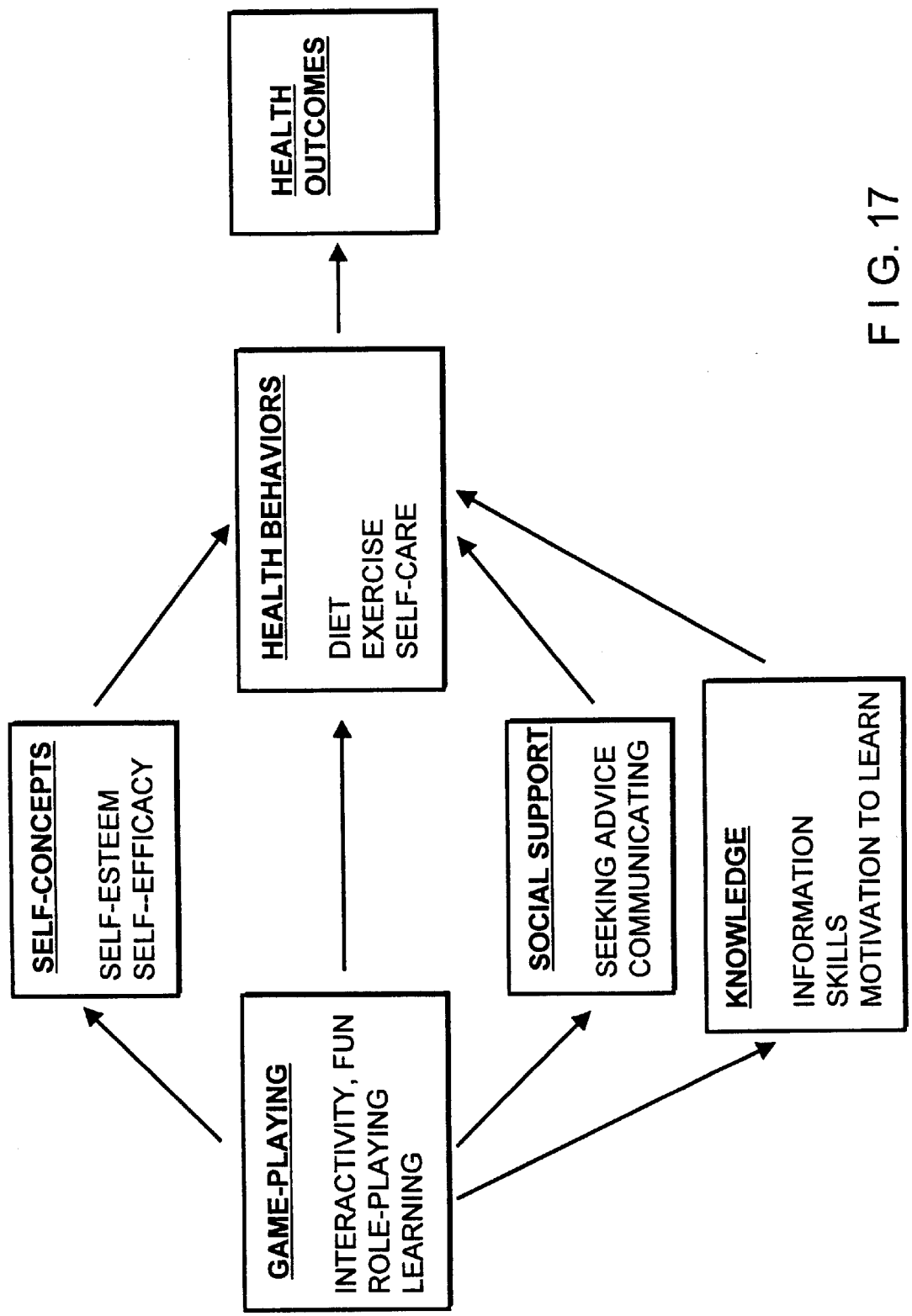
FIG. 17 is a detailed flowchart for the ADHD video game according to the present invention.

Embodiments of the invention for diagnostic assessment for ADHD can also include programming for conduction of continuous performance tests that include distractions. For example, as is shown in FIG. 16, a fluttering butterfly 210 or other moving object such as a hopping frog or flying saucer can be generated in the peripheral region of the video display to provide a measure of the patient's degree of distractibility. During audio continuous performance tests synthesized voice signals such as "Now!" "or" "Go!" can be generated by microprocessor-based unit 110 (FIG. 3). In situations in which synthesized voice is beyond the capability of the sound generator being used, the micro-processor-based unit 110 can supply various distractive sounds or noises.

When the battery of diagnostic assessments is established by a clinician, program instructions can be stored in external memory unit 112 (FIG. 3) or otherwise provided to a microprocessor-based unit, to determine the number of continuous performance tests to be performed and the type of each test (i.e. video without distractions; video with distractions; audio without distractions; and audio with distractions). The sequence of the tests, both with respect to one another and with respect to the previously discussed delayed reaction tests, is also determined by the clinician. For each continuous performance test, the clinician can select the total number of target and non-target stimuli to be presented; the test duration; and the minimum stimulus duration (which is typically set at around 100 milliseconds). Diagnostic measures that are recorded in external memory unit 112 during conduction of continuous performance tests include: the number of target stimuli correctly identified (i.e. captured); the number of target stimuli for which the user failed to react (missed stimuli); the number of non-target stimuli for which there was a response; the number of times the button or switch was activated after a stimulus passed (late hits); and the final interstimulus interval (and/or the minimum interstimulus interval attained during the test).

As was described relative to FIGS. 3 and 4, program instructions for establishing the diagnostic assessment procedure (e.g. storing suitable program instructions in external memory 112) and retrieval of signals representative of the diagnostic measures gathered during diagnostic testing (e.g. accessing information stored in external memory 112) are performed by executing an administrator program with the clinician's computer (122 in FIG. 3; digital signal processing unit 142 in FIG. 4). When the administrator program of the current realizations of the intention is executed, a main menu screen is displayed, allowing the clinician to select menu items that include: the opening of a new file (i.e. establishing a diagnostic assessment procedure for a new patient or subject); opening an existing file; saving a file (storing a diagnostic assessment configuration in memory of the clinician's computer); closing a file; and producing the diagnostic assessment procedure (i.e. storing the appropriate program instructions in an external memory 112 or, alternatively, initiating execution of a diagnostic assessment procedure with a micro-processor-based unit 110 that is directly connected to the clinician's computer (FIG. 4).

Presented herein is a method for treating medical conditions in human patients using a micro-processor-based video game. This method gives a better picture of the ailment through its standardized scoring procedure and makes the treatment much less costly by considerably reducing the number of therapy sessions with the physician or health care professional. In addition, video games emphasize superior treatment in the patient's own environment. This leads to self-help responses difficult to foster in therapy sessions. The patient recognizes the importance of medications and treatment regimens in an entertaining manner. Moreover, the patient participates actively in the treatment by following instructions embedded in the video game or even generating positive physiological responses due to stimuli presented in the video game.

The method of the invention also provides a treatment to which the patient can resort as the need arises. The intrinsic fun in playing video games ensures higher treatment compliance for all patients, and in particular children. The self-treatment instructions communicated by this method can be used to additionally induce patients to independently perform measurements of physical parameters associated with their medical condition.

Finally, the scoring of the video game provides an excellent standardized measure for evaluating treatment results and improving continued treatment. In carrying out the method the micro-processor-based system can be expanded to use any number of communications devices, monitoring set-ups, and other state-of-the-art medical equipment. Therefore, the scope of the invention should be determined, not by examples given, but by the appended claims and their substantial equivalents.

Various modifications and alterations to the present invention may be appreciated based on a review of this disclosure. These changes and additions are intended to be within the scope and spirit of this invention as defined by

What is claimed is:

1. A microprocessor controlled video game system adapted to receive commands generated by a user suffering a psychological disorder, said system generating complex multidimensional information displays as a first series of outputs to the user in the form of indicia configured and presented in a manner directed to aid in the diagnosis of said psychological disorder, the system comprising:

means for controlling said system using a stored protocol directed to said psychological disorder, said protocol comprised of display controlling functions wherein said functions include programming commands for controlling one or more graphical elements presented on said displays;

means for inputting said user generated commands into said system wherein said user generated commands are interactively entered by said user in response to said first series of outputs to said user; and means for relaying a second series of outputs to a health care professional, wherein said second series of outputs are specifically configured to provide a presentation of the user's inputs to said health care professional for diagnosing said psychological disorder.

2. The system of claim 1, wherein said protocol of display controlling functions includes programming commands for manipulating at least one graphical character presented on said displays.

3. The system of claim 1 further comprising:

means for linking said system to a network, said linking means comprising a means for interfacing said microprocessor to said network; and at least one peripheral server linked to said network, said server adapted to receive said inputs and said outputs, and adapted to excahange data within said network.

4. The system of claim 3, wherein said server comprises:

means for receiving said inputs and said outputs;

means for storing said inputs and said outputs; and means for processing said inputs and said outputs, further comprised of a second microprocessor controlled data processing unit in communication with said system, wherein said second microprocessor controlled data processing unit is adapted to process and exchange data with said system.

5. The system of claim 1, wherein said psychological disorder for diagnosis is selected from the group consisting of ADHD, schizophrenia, depression, hyperactivity, phobias, panic attacks, anxiety, overeating, compulsive behaviors, addictiions and substance abuse.

6. The system of claim 1, wherein said stored protocol is specifically configured to provide a test battery of continuous performance tasks to said user through said displays, and wherein said system further comprises a data collection sub-system for storing and analyzing said user's inputs responsive to said battery and relaying the analytic results via said second series of outputs to said health care professional for diagnosing said psychological disorder.

7. The system of claim 6, wherein said psychological disorder for diagnosis is ADHD, said battery further comprises auditory and visual delayed reaction time tests for attention, and wherein said subsystem comprises an administrator program for configuring said tests.

8. A method for diagnosing a psychological disorder in a human patient comprising the steps of:
   a) encoding electronic instructions for an interactive video game configured for said psychological disorder and comprised of a microprocessor controlled system adapted to receive input data from said patient and adapted to provide an interactive display to said patient, said system further comprising a stored protocol directed to diagnosis criteria for said psychological disorder;
   b) loading said electronic instructions into said microprocessor-based system;
   c) instructing said human patient on how to use said micro-processor-based unit to play said interactive video game; and
   d) collecting said input data from said patient and analyzing said data based on said protocol to arrive at said diagnosis.

9. The method of claim 8, wherein said psychological disorder for diagnosis is selected from the group consisting of ADHD, schizophrenia, depression, hyperactivity, phobias, panic attacks, anxiety, overeating, compulsive behaviors, addictiions and substance abuse.

10. The method of claim 8, wherein said stored protocol is specifically configured to provide a test battery of continuous performance tasks to said patient through said interactive display, and wherein said input data from said patient responsive to said test battery is analyzed for diagnosing said psychological disorder.

11. The method of claim 10, wherein said psychological disorder for diagnosis is ADHD, said battery further comprises auditory and visual delayed reaction time tests for attention.

12. The method of claim 11, wherein said protocol analyzes said input data from said patient to categorize whether said patient is responsive to maintenance psychostimulants.

13. A microprocessor controlled video game system adapted to receive commands generated by a user suffering a psychological disorder, said system generating multidimensional information displays as outputs utilizing indicia on said displays configured and presented in a manner directed to the treatment of said psychological disorder, the system comprising:
   means for controlling said system using a stored protocol directed to said psychological disorder, said protocol comprised of display controlling functions wherein said functions include programming commands for controlling one or more graphical elements presented on said displays;
   means for inputting said user generated commands into said system wherein said user generated commands are interactively entered by said user in response to said outputs presented on said displays; and
   means for interpreting said inputted user generated commands, applying said stored protocols to said inputted user generated commands and based thereon, controlling said output to said display wherein said output is specifically configured to provide a presentation to said user that enhances the treatment of said psychological disorder.

14. The system of claim 13, wherein said protocol of display controlling functions includes programming commands for manipulating at least one graphical character presented on said displays.

15. The system of claim 13, wherein said psychological disorder for treatment is selected from the group consisting of ADHD, schizophrenia, depression, hyperactivity, phobias, panic attacks, anxiety, overeating, compulsive behaviors, addictiions and substance abuse.

16. The system of claim 13, wherein said stored protocol is configured to provide experiential education specific for said psychological disorder.

17. The system of claim 14, wherein said psychological disorder for treatment is ADHD, and said stored protocol is configured to provide opportunities to practice focus of attention and control of impulses, supportive and performance feedback, and general information about ADHD and its treatment.

18. A method for treatment of a psychological disorder in a human patient comprising the steps of:
   a) providing said patient with a microprocessor controlled video game adapted to interact with said patient to obtain personal data related to said psychological disorder;
   b) transmitting said personal data to a microprocessor controlled system, said system adapted to collect and analyze said data;
   c) compiling a report based on said collected and analyzed data; and
   d) identifying criteria specific to said patient and implementing a treatment regimen for said psychological disorder.

19. The method of claim 18, wherein said psychological disorder for treatment is selected from the group consisting of ADHD, schizophrenia, depression, hyperactivity, phobias, panic attacks, anxiety, overeating, compulsive behaviors, addictiions and substance abuse.

20. The method of claim 19, wherein said psychological disorder for treatment is ADHD, and said treatment regimen includes management of psychostimulant medication.

21. A method for monitoring a psychological disorder in a human patient comprising the steps of:
   a) encoding electronic instructions for an interactive video game configured for said psychological disorder and comprised of a microprocessor controlled system adapted to receive input data from said patient and adapted to provide an interactive display to said patient, said system further comprising a stored protocol directed to criteria for monitoring said psychological disorder;
   b) loading said electronic instructions into said microprocessor-based system;
   c) instructing said human patient on how to use said micro-processor-based unit to play said interactive video game; and
   d) monitoring said input data from said patient.

22. The method of claim 21, wherein said psychological disorder for monitoring is selected from the group consisting of ADHD, schizophrenia, depression, hyperactivity, phobias, panic attacks, anxiety, overeating, compulsive behaviors, addictiions and substance abuse.

23. The method of claim 21, wherein said stored protocol is specifically configured to provide a test battery of continuous performance tasks to said patient through said interactive display, and wherein said input data from said patient responsive to said test battery is monitored to facilitate diagnoses and treatment of said psychological disorder.

* * * * *